US009182396B2

(12) United States Patent
Olson et al.

(10) Patent No.: US 9,182,396 B2
(45) Date of Patent: Nov. 10, 2015

(54) LATERAL FLOW IMMUNOASSAY FOR COMPLEMENT ACTIVATION AND METHODS OF USE FOR POINT-OF-CARE ASSESSMENT OF COMPLEMENT-ASSOCIATED DISORDERS

(75) Inventors: Paul Olson, St. Louis, MO (US); Don W. Moss, Louisville, KY (US)

(73) Assignee: Kypha, Inc., St. Louis, MO (US)

( * ) Notice: Subject to any disclaimer, the term of this patent is extended or adjusted under 35 U.S.C. 154(b) by 143 days.

(21) Appl. No.: 13/287,432

(22) Filed: Nov. 2, 2011

(65) Prior Publication Data

US 2012/0141457 A1 Jun. 7, 2012

Related U.S. Application Data

(60) Provisional application No. 61/409,297, filed on Nov. 2, 2010.

(51) Int. Cl.
*A61K 39/395* (2006.01)
*G01N 33/00* (2006.01)
*G01N 33/53* (2006.01)
(Continued)

(52) U.S. Cl.
CPC .......... *G01N 33/564* (2013.01); *G01N 33/558* (2013.01); *G01N 33/86* (2013.01); *G01N 2333/4716* (2013.01); *G01N 2800/125* (2013.01); *G01N 2800/26* (2013.01)

(58) Field of Classification Search
CPC ... G01N 33/564; G01N 33/558; G01N 33/86; G01N 2333/4716; G01N 2800/125; G01N 2800/26
See application file for complete search history.

(56) References Cited

U.S. PATENT DOCUMENTS 6,316,604 B1 * 11/2001 Fearon et al. ................. 530/416
7,371,582 B2 * 5/2008 Nahm et al. .................. 436/514
(Continued)

FOREIGN PATENT DOCUMENTS

WO WO-2005/078442 8/2005
WO WO 2005078442 A1 * 8/2005
(Continued)

OTHER PUBLICATIONS

Vladutiu et al., (Clin Chem. 1976. 22(2):267-269).*
(Continued)

*Primary Examiner* — Cherie M Stanfield
(74) *Attorney, Agent, or Firm* — Choate, Hall & Stewart LLP

(57) ABSTRACT

A method for treating an individual at risk for a complement-associated disorder is provided, including: (a) obtaining a sample of a body fluid from the individual; (b) measuring a complement activation level in the sample via a point-of-care lateral flow immunoassay; (c) correlating the complement activation level in the sample to a risk of a complement-associated disorder by comparing the complement activation level in the sample to a reference level in a control, wherein a deviation in complement activation level in the sample compared to the reference level in the control indicates the individual is at risk for a complement-associated disorder; (d) selecting a treatment for the individual, based on the correlating of step (c); and (e) treating the individual with the treatment selected in accordance with step (d). Lateral flow immunoassays and a method of monitoring an individual suffering from a complement-associated disorder are also provided herein.

28 Claims, 19 Drawing Sheets

(51) Int. Cl.
*G01N 33/566* (2006.01)
*G01N 33/564* (2006.01)
*G01N 33/558* (2006.01)
*G01N 33/86* (2006.01)

(56) References Cited

U.S. PATENT DOCUMENTS

| | | | |
|---|---|---|---|
| 7,910,381 B2 | 3/2011 | Ford et al. | |
| 2006/0292700 A1* | 12/2006 | Wang et al. | 436/514 |
| 2007/0224703 A1 | 9/2007 | Nayeri et al. | |

FOREIGN PATENT DOCUMENTS

| | | |
|---|---|---|
| WO | WO-2006/124888 | 11/2006 |
| WO | 2010/135717 A2 | 11/2010 |
| WO | WO 2010135717 A2 * | 11/2010 |

OTHER PUBLICATIONS

Sahu et al., (Immun Rev. 2001. 180:35-48).*
International Search Report and Written Opinion dated Mar. 12, 2012, issued in corresponding PCT Intl. Appln. No. PCT/US11/058945.
Catania et al., "Immunological consequences of trauma and shock", Ann. Acad. Med. Singapore, 28:120-132 (1999).
Emlen et al., "Therapeutic complement inhibition: new developments", Semin. Thromb. Hemost., 36(6):660-668 (2001).
Hecke et al., "Circulating complement proteins in multiple trauma patients—correlation with injury severity, development of sepsis, and outcome", Crit. Care Med., 25(12):2015-2024 (1997).
Huber-Lang et al., "Complement-induced impairment of innate immunity during sepsis", J. Immunol., 169:3223-3231 (2002).
Kang et al., "Change of complement system predicts the outcome of patients with severe thermal injury", J. Burn Care Rehabil., 24:148-153 (2003).
Ricklin et al., "Complement-targeted therapeutics", Nat. Biotechnol., 25(11):1265-1275 (2007).
Wagner et al., "Therapeutic potential of complement modulation", Nat. Rev. Drug Discov., 9(1):43-56 (2010).
Younger et al., "Detrimental effects of complement activation in hemorrhagic shock", J. Appl. Physiol., 90:441-446 (2001).
Zilow et al., "Complement activation and the prognostic value of C3a in patients at risk of adult respiratory distress syndrome", Clin. Exp. Immunol., 79:151-157 (1990).
Palarasah et al., Generation of a C3c specific monoclonal antibody and assessment of C3c as a putative inflammatory marker derived from complement factor C3, J. Immunol. Methods, 362:142-150 (2010).
Vladutiu, A. O. et al, Complement C3 in serum and plasma, as measured by radial immunodiffusion with four commercial kits, Clin. Chem., 22(2):267-269 (1976).
International Search Report and Written Opinion for PCT/US13/38897, mailed Dec. 2, 2013.

* cited by examiner

The complement cascade

C3 is activated and deactivated by protease activity

Antibody pairs that recognize either intact C3 or iC3b

Single analyte lateral flow immunoassay test cassettes

Double analyte lateral flow immunoassay test cassettes in parallel

Triple analyte lateral flow immunoassay test cassettes in parallel

Single and double lateral flow immunoassay membrane strips in series

Multiple analyte lateral flow immunoassay test cassettes in series iC3b lateral flow immunoassay cassette sensitivity Intact C3 lateral flow immunoassay cassette sensitivity

Figure 14
Cross talk between intact C3 and iC3b in lateral flow immunoassays

| Ratio of intact C3:iC3b | Total iC3b output signal | | Fractional contribution of intact C3 to iC3b signal | |
|---|---|---|---|---|
| | (H08K-01) | (J24K-03) | (H08K-01) | (J24K-03) |
| 2000 to 1 | 2.16 | 5.12 | 1.16 | 4.12 |
| 1000 to 1 | 1.79 | 4.98 | 0.79 | 3.98 |
| 500 to 1 | 1.67 | 4.69 | 0.67 | 3.69 |
| 250 to 1 | 1.31 | 3.55 | 0.31 | 2.55 |
| 125 to 1 | 1.24 | N/A | 0.24 | N/A |
| 0 to 1 | 1.00 | 1.00 | 0.00 | 0.00 |

C3 and iC3b levels in basal tears from a single individual at 12 hour intervals

Intact C3 and iC3b levels in whole blood from a healthy individual

Intact C3 and iC3b levels in whole blood from a healthy individual

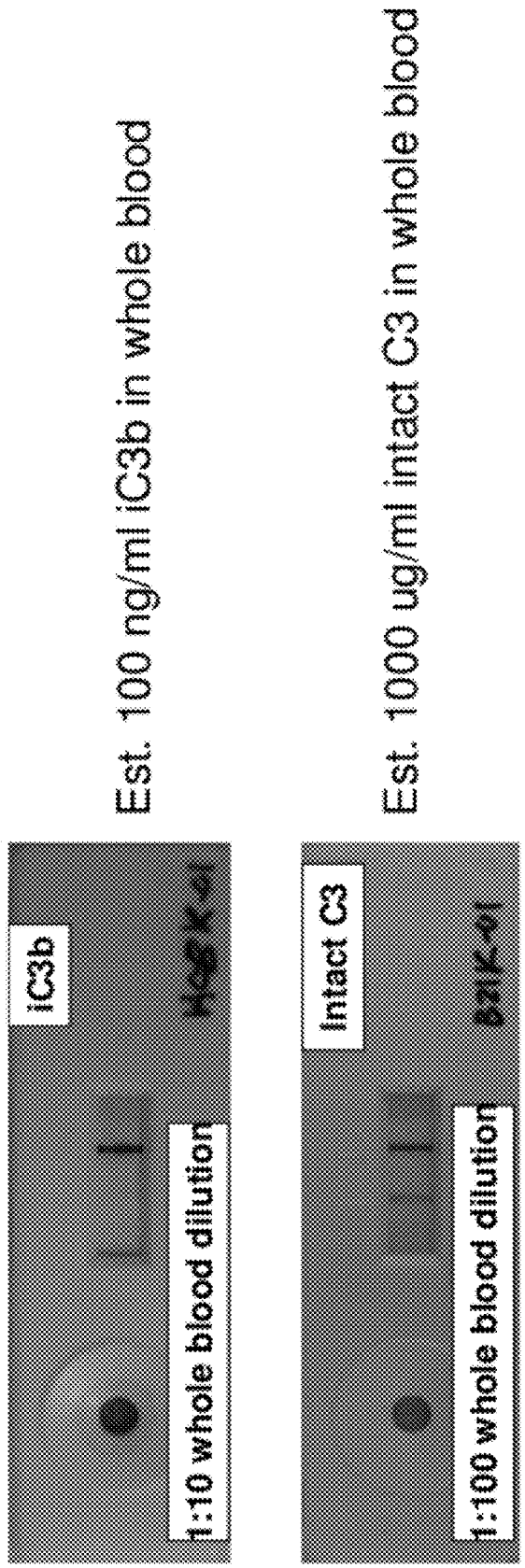

Figure 19

| Body Fluid | Known Source of Complement Component C3 | Validated by ELISA or LFA | Control / Normal / Healthy | Compromised (Disease / Sick) | Inflammatory diseases where C3 biomarkers have been or are expected to be present |
|---|---|---|---|---|---|
| Whole blood | Yes | Yes | Intact C3, iC3b | Intact C3, iC3b | Infections, autoimmune diseases (RA, MS, psoriasis, Crohn's, lupus, etc.), trauma, myocardial infarction, stroke, heart disease, diabetes, liver fibrosis, kidney disease, organ transplant/rejection, cancer, food allergies |
| Plasma | Yes | Yes | Intact C3, iC3b | Intact C3, iC3b | |
| Serum | Yes | Yes | Intact C3, iC3b | Intact C3, iC3b | |
| Cerebral spinal fluid | Yes | Yes | Intact C3, iC3b | Intact C3, iC3b | Trauma, Alzheimer's, Parkinson's, Multiple Sclerosis, Amyotrophic lateral sclerosis (ALS), infections |
| Tear | Yes | Yes | Intact C3, iC3b | Intact C3, iC3b | Age-related macular degeneration (AMD), Dry eye disease (DED), infections |
| Wound exudate | Yes | Yes | | Intact C3, iC3b | Trauma, burns, various ulcers, infections |
| Mucous secretion (nasal) | Yes | Yes | Intact C3, iC3b (healthy but may be suffering from minor seasonal allergies) | | Infection |
| Cerumen (earwax) | | iC3b only | Not Detected | | Otitis media with effusion (OME) |
| Sebum (skin oil from sebaceous glands), lesions, or skin in general | | iC3b only | Not Detected (forearm rub) | | Acne, cold sores |
| Saliva | | iC3b only | Not Detected | | Periodontal disease, canker sores |
| Urine | | Yes | Not Detected | | Glomerulonephritis, infection |
| Sweat | | | | | |
| Semen | | | | | Silent male genital tract infection |
| Vaginal fluid | | | | | Infection |
| Breast milk | | | | | Infection |
| Breath condensate | | | | | Asthma, COPD, emphysema, cystic fibrosis |

LATERAL FLOW IMMUNOASSAY FOR COMPLEMENT ACTIVATION AND METHODS OF USE FOR POINT-OF-CARE ASSESSMENT OF COMPLEMENT-ASSOCIATED DISORDERS

RELATED APPLICATION

This application claims priority under 35 U.S.C. §119(e) to U.S. Provisional Application Ser. No. 61/409,297, filed Nov. 2, 2010, the contents of which are incorporated by reference herein in their entirety.

FIELD OF THE INVENTION

The presently disclosed subject matter relates to lateral flow immunoassays for the measurement of complement activation. Specifically, the presently disclosed subject matter relates to a lateral flow immunoassay for the quantitative measurement of intact C3 and iC3b in a sample and methods of using the same in the evaluation and treatment of individuals at risk for complement-associated disorders such as inflammatory distress.

BACKGROUND

Inflammation is the physiological response of vascularized tissue to injury, infection, and certain diseases. The inflammatory process is a biological requirement for wound healing after traumatic injury and for the clearance of infection. However, inflammation can also damage self-tissue. For this reason, inflammation is often considered a double-edged sword.

Complement is the most ancient arm of the immune system and is deeply rooted in the inflammatory process. The complement protein cascade is a first line of defense against invading microbes and a critical player in the wound healing process. The complement cascade comprises more than 30 serum and cellular proteins and plays important roles in innate and adaptive immunity. Complement activation can occur via three major pathways: the classical, alternative, and lectin pathways. All three major pathways of complement activation converge on the central protein complement component 3 (C3). C3 is a central mediator of inflammation and is activated by most factors that cause inflammation. FIGS. 1 and 2 provides schematic overviews of C3 and its activation products.

Complement, and C3 in particular, is associated with several disease indications, both acute and chronic. Examples include, but are not limited to, trauma, respiratory distress, sepsis, other forms of infection, infectious diseases (e.g., hemorrhagic fevers), multiple organ failure, age-related macular degeneration, rheumatoid arthritis, systemic lupus erythematosus, glomerular nephritis, ischemia/reperfusion injury, inflammatory bowel disease, intracranial hemorrhage, myocardial infarction, and cardiac arrest.

Severe trauma patients present unique clinical challenges. Accurate assessment of injury severity is important for initial intervention and patient stabilization, as well as patient triage (e.g., following mass casualty incidents). Those patients admitted to the ICU, even after initial stabilization, remain at high risk for secondary life-threatening complications involving organ dysfunction, respiratory distress and sepsis, among others. Many of these conditions involve hyper-inflammatory events that can escalate rapidly and cause significant damage before clinical symptoms are detected. These events are generally preceded by an increasingly unstable homeostasis of the inflammatory response. The ability to monitor inflammation frequently (e.g., every hour or two) and reliably at the earliest time points following injury has tremendous clinical value and would improve clinical outcomes for critical care patients.

Several reports have shown that complement activation occurs immediately after injury and correlates with severity of injury. In one study, circulating levels of complement protein in trauma patients were found to correlate with patient outcome. See Hecke, et al., *Circulating complement proteins in multiple trauma patients—correlation with injury severity, development of sepsis, and outcome,* Crit. Care Med. 25(12): 2015-24 (1997). In this study, the authors measured the plasma concentrations of both C3a and total C3 directly after the injury and in the ICU in the days following injury. They detected evidence of complement C3 activation at the earliest time points following injury. However, complement activation was more pronounced in non-survivors than survivors for the first eight hours. At the earliest time points, the degree of C3 activation correlated with patient outcome. Hecke et al. also found the ratio of the C3 split product, C3a, when taken as a ratio to total complement, was a better predictor of outcome than C3a alone.

A similar study by Zilow, et al., *Complement activation and the prognostic value of C3a in patients at risk of adult respiratory distress syndrome,* Clin. Exp. Immunol. 79: 151-57 (1990), retrospectively found that monitoring of C3a and total C3 at frequent (6 hr) intervals might be useful for identifying patients at high risk for or in the early stages of respiratory distress. These investigators drew the first plasma sample within 2 hours of injury and repeated 6 hour samplings for the first 48 hours and then at daily intervals thereafter. Zilow et al. found a significant correlation between C3a levels and C3a:total C3 ratio at 6 and 12 hours, as a well as from 5 days outward.

In the field of trauma care, the first hour after injury is sometimes referred to as the "Golden Hour." While not desiring to be bound by theory, it is generally believed that intervention within the first hour after traumatic injury greatly increases the outcome of the patient. Better diagnostic information provided earlier would help improve the critical care specialist's intuition when making treatment decisions.

Heretofore, a point-of-care assay for measuring complement activation within the actionable window of treatment has not been known in the art. Although the associations between complement and disease or trauma have long been recognized, C3 is monitored in only a small number of diseases or conditions. Even in those instances, current assay methods have limitations. First, in most cases, traditional complement assays are directed to total C3 as the target analyte (for example, via turbidity assays and ELISA). Total C3 is a combination of intact (or native) C3 and C3 activation and deactivation products. These tests generally detect decreases in circulating C3 levels. Decreased levels of total C3 therefore only measure C3 depletion due to massive activation. However, other factors such as diet or exercise can cause lower steady state levels of C3. As total C3 assays do not measure turnover, the causes of activation cannot be distinguished. Furthermore, a test that measures total C3 cannot monitor the real-time changes in C3 activation signature that would be useful in directing patient care. For example, patients suffering from trauma or systemic lupus (marked by decreased C3 levels) would benefit from improved C3 activation monitoring. Currently, treatment effectiveness for systemic lupus is measured by a return of depressed C3 levels to normal levels. However, the physician has difficulty in discerning whether the underlying disease process has been halted or just retarded sufficiently for homeostatic mechanisms to return C3 to physiologically normal levels.

A second limitation in current C3 testing is the time required to perform most assays. A typical ELISA assay for the detection of complement activation requires hours to perform and the ready availability of a laboratory and a skilled technician. This assay platform is therefore not useful for indications of inflammatory dysfunction, in which biomarkers change on the order of minutes and clinical intervention is required on a similar timescale.

A third limitation in current C3 testing lies in the nature of the protein cascade itself. Complement is notoriously fastidious and can become activated by virtue of standard analysis procedures (handling, storage, and exposure to foreign materials that contact C3 during analysis). Complement is very effective at lysing invading microbes and initiating the wound healing response at sites of injury. This effectiveness is due in part to the ability of C3 to be activated by foreign materials such as bacterial cell wall components. While this property is useful in directing an immune response to new foreign pathogens, this same property presents formidable challenges to experimental and diagnostic study. Materials such as plastics used in sample handling, manipulation of the sample itself, and improper storage conditions can also trigger complement activation. The more processing and handling steps required to perform a given assay, the more false positives can be expected, due to activation of complement by virtue of the assay itself. These false positives complicate traditional testing and render current testing methods unsuitable for use in directing patient care in near real-time.

A further consideration in complement activation testing is the selection of the best biomarker for detecting real time changes in the inflammatory response. C3 has several attractive qualities as a biomarker in inflammation. First, as the central protein of the complement system, C3 is activated by most stimuli that will cause complement activation. Second, C3 activates in proportion to the degree of injury or infection. Third, C3 responds in near real-time to a physiological insult. Complement activation occurs in direct response to an agent causing crisis, in contrast to other acute phase inflammatory markers that take hours or days to respond. This rapid response property is not present in other biomarkers frequently used in the clinic.

Specifically, intact (or native) C3 is a valuable marker of inflammatory status. Intact C3 represents the amount of C3 available for activation. Total C3 represents intact C3 as well as all C3 activation products. At present, standard complement assays generally measure total C3 via turbidity assays or ELISA. Although technically easier to perform, total C3 assays cannot detect C3 depletion as accurately as intact C3 assays. Monitoring intact C3, especially over time, is useful for following massive complement activation events, such as those that occur in trauma and other systemic complement activation indications. Monitoring intact C3 over time allows a clinician to detect the onset of an immunosuppressive state caused by depletion of C3. Further, intact C3 may be more useful than total C3 when calculating complement activation indexes (e.g., the C3a:total C3 ratio used by Zilow and Hecke). Intact C3 assays have historically proven difficult to administer or depend upon, in part because intact C3 is very labile and can denature or self-activate if not handled properly.

The C3 split product, iC3b, is also a valuable marker of inflammatory response. iC3b has a half-life of 30 to 90 minutes, serving as a less volatile (e.g., compared to C3a), but still rapidly responsive biomarker. However, iC3b is present at much lower levels than intact C3 in patient samples. Even a small degree of cross-talk (for example 1%) between intact C3 protein and the iC3b-specific assay produces a false positive iC3b signal at a level twice that of normal circulating iC3b. Hence, while a desirable marker of inflammation, heretofore iC3b has posed significant challenges in diagnostic testing.

WO 2010/135717, by Zhang et al., published Nov. 25, 2010, is directed to methods for assessing complement activation via the biomarkers intact C3, iC3b, and total C3. However, Zhang et al. is limited to traditional sandwich-type immunoassays such as ELISA, requiring laboratory processing and the expertise of skilled technicians. Further, the assays and methods of Zhang et al. require sample preparation, storage, and handling steps that are known to activate the labile intact C3 produce false positive test results, impeding the ability to accurately measure intact C3. Moreover, the assays and methods of Zhang et al. require hours to process and are thus incapable of providing the near real-time data that can impact patient care in the earliest time points after physiological crisis.

The need persists for a rapid, point-of-care assay for the measurement of intact C3 and iC3b in a patient at risk for a complement-associated disorder which minimizes complement activation due to sample handling and allows a clinician to act upon changes in complement activation levels in near real-time, in order to guide patient treatment and monitor inflammatory response.

SUMMARY OF THE INVENTION

The present inventors have now developed a point-of-care method and assay for the qualitative and quantitative measurement of intact C3 and iC3b suitable for use in directing patient care at the earliest time points immediately following traumatic injury or other physiological crises. By carefully selecting capturing and detecting antibody pairs that avoid interfering cross-talk and applying the technology to a lateral flow immunoassay platform, the inventors have surprisingly found that it is possible to detect and quantify the biomarkers intact C3 and iC3b, while avoiding the false positive results that have plagued more conventional testing methods for these analytes.

Accordingly, a method for treating an individual at risk for a complement-associated disorder is provided herein, the method comprising: (a) obtaining a sample of a body fluid from the individual; (b) measuring a complement activation level in the sample via a point-of-care lateral flow immunoassay; (c) correlating the complement activation level in the sample to a risk of a complement-associated disorder by comparing the complement activation level in the sample to a reference level in a control, wherein a deviation in complement activation level in the sample compared to the reference level in the control indicates the individual is at risk for a complement-associated disorder; (d) selecting a treatment for the individual, based on the correlating of step (c); and (e) treating the individual with the treatment selected in accordance with step (d).

In another embodiment, a lateral flow immunoassay for the point-of-care detection of a marker of complement activation in a body fluid sample comprising complement proteins is provided, the lateral flow immunoassay comprising: a membrane strip; a detecting antibody that binds a first epitope of the marker; a test line comprising a capturing antibody that binds a second epitope of the marker; and a control line comprising an antibody that binds a control analyte, wherein the marker is selected from the group consisting of intact C3 and iC3b.

In still another embodiment, a lateral flow immunoassay for the point-of-care detection of markers of complement activation in a body fluid sample comprising complement proteins, the lateral flow immunoassay comprising: a membrane strip; a first detecting antibody that binds a first epitope of intact C3; a first test line comprising a first capturing antibody that binds a second epitope of intact C3; a second detecting antibody that binds a first epitope of iC3b; a second test line comprising a second capturing antibody that binds a second epitope of iC3b; and at least one control line comprising an antibody that binds a control analyte.

In another embodiment, a method for monitoring an individual who is receiving treatment for a physiological condition and who is suffering from a complement-associated disorder is provided, the method comprising: (a) obtaining serial samples of a body fluid from the individual; (b) determining a complement activation level in each of said samples via a point-of-care lateral flow immunoassay; (c) comparing the complement activation levels in the serial samples to detect a change in a complement activation level over time; and (d) modifying treatment for the individual, based on the correlating of step (c).

These and other objects, features, embodiments, and advantages will become apparent to those of ordinary skill in the art from a reading of the following detailed description and the appended claims.

BRIEF DESCRIPTION OF THE DRAWINGS

FIG. 14 shows crosstalk between intact C3 and iC3b antibodies in lateral flow immunoassays.

FIG. 18 shows intact C3 and iC3b levels in a normal individual 2 hours after heavy exertion (100 mile bicycle ride). Results show greater than 1000-fold more intact C3 than iC3b in whole blood from a healthy individual post-exertion.

FIG. 19 is a table of exemplary body fluids suitable for use with the assays and methods disclosed herein.

DETAILED DESCRIPTION OF THE INVENTION

Figure 1:
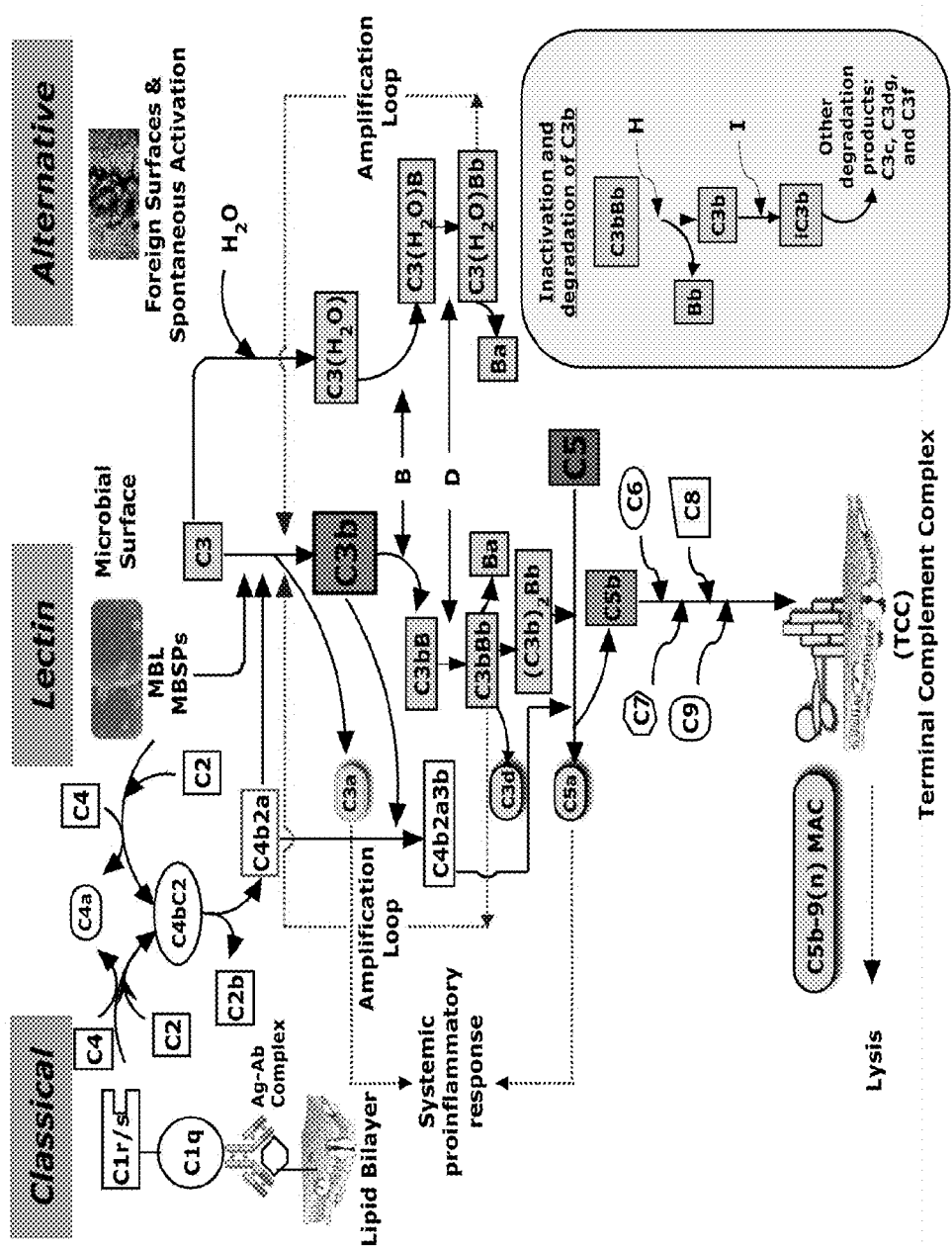
FIG. 1 provides a schematic overview of the complement system. Complement is activated by three major pathways, all of which converge on the activation of intact C3. Proteolytic activation of C3 produces the C3 split products C3a and C3b. C3b is further proteolytically modified to form iC3b, a biomarker for C3 activation. Intact C3 and iC3b are circled in the schematic.

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

"Analyte" means any entity, particularly a chemical, biochemical or biological entity to be assessed, e.g., whose amount (e.g., concentration or mass), activity, composition, or other property(ies) is/are to be detected, measured, quantified, evaluated, analyzed, etc. An "analyte" can be a single molecular species or can be composed of multiple distinct molecular species.

"Antibody" encompasses intact and/or full length immunoglobulins of types IgA, IgG (e.g., IgG1, IgG2, IgG3, IgG4), IgE, IgD, IgM, IgY, antigen-binding fragments or single chains of complete immunoglobulins (e.g., single chain antibodies, Fab fragments, F(ab')2 fragments, Fd fragments, scFv (single-chain variable), and dAb fragments), and other proteins that include at least one antigen-binding immunoglobulin variable region, e.g., a protein that comprises an immunoglobulin variable region, e.g., a heavy (H) chain variable region (VH) and a light (L) chain variable region (VL). The light chains of an antibody may be of type kappa or lambda. An antibody may be polyclonal or monoclonal. A polyclonal antibody contains immunoglobulin molecules that differ in sequence of their complementarity determining regions (CDRs) and, therefore, typically recognize different epitopes of an antigen. Often a polyclonal antibody is derived from multiple different B cell lines each producing an antibody with a different specificity. A polyclonal antibody may be composed largely of several subpopulations of antibodies, each of which is derived from an individual B cell line. A monoclonal antibody is composed of individual immunoglobulin molecules that comprise CDRs with the same sequence, and, therefore, recognize the same epitope (i.e., the antibody is monospecific). Often a monoclonal antibody is derived from a single B cell line or hybridoma. An antibody may be a "humanized" antibody in which for example, a variable domain of rodent origin is fused to a constant domain of human origin or in which some or all of the complementarity-determining region amino acids often along with one or more framework amino acids are "grafted" from a rodent, e.g., murine, antibody to a human antibody, thus retaining the specificity of the rodent antibody.

In another embodiment, the capturing and/or detecting agents include other ligands, such as natural receptors for activated C3 (e.g., complement receptors 1, 2, and 3), aptamers, peptides, other small molecule ligands, and the like.

An aspect of certain embodiments of the invention is the selection of antibodies for use as capture and detection agents. The inventors discovered that many published and commercially available antibodies exhibited crosstalk between intact C3 and various C3 cleavage products or between different C3 cleavage products. For example, certain monoclonal antibodies against human C3a show significant and unexpected cross-reactivity with C3b and iC3b. It was recognized that cross-reactivity could be a significant source of inaccuracy in certain situations. Of particular concern in developing an assay for iC3b was crosstalk between intact C3 and iC3b observed with many of the iC3b antibodies tested. Further testing showed that crosstalk between C3b and iC3b was even more significant with at least some of these antibodies. This was of concern because iC3b levels are expected to be present at much lower levels than intact C3 in patient samples. One aspect of certain embodiments of the invention is the selection of antibodies with specificity for intact C3 or iC3b so as to minimize such crosstalk. In certain embodiments, antibodies with specificity for intact C3 or iC3b are not substantially cross-reactive. In this context, "not substantially cross-reactive" means less than about 0.1% cross-reactive, meaning that a 1 ug/ml solution of C3 must register as less than about 1 ng/ml of iC3b. The about 0.1% threshold is based on the physiological levels of intact C3 and iC3b in a normal individual. Normal iC3b levels are approximately 0.5% that of total C3 in circulation. If C3 crosstalk contributes more than about 25% to the iC3b signal in a complement activation assay, the assay can produce false positive results that abrogate the utility of the assay.

"Body fluid" means any fluid in the body that may be assayed for complement activation. Body fluids include, but are not limited to, whole blood, serum, plasma, urine, tears, saliva, wound exudate, broncheoalveolar lavage fluid, and cerebrospinal fluid. See FIG. 19 for a non-limiting list of suitable body fluids.

"Complement activation level" means the amount of complement (generally C3) that is activated at a given time point. Amounts (i.e., levels) of intact C3, iC3b, and/or total C3 are typically expressed in terms of concentration but may be expressed in terms of mass or weight. Concentration may be expressed in various ways, e.g., in terms of molarity, molality, mole fraction, mass fraction (mass of a substance in a mixture as a fraction of the mass of the entire mixture), mass per unit volume, etc. For purposes of description herein, concentration (e.g., mass per unit volume) will generally be used. Complement activation level can also be described as a ratio of iC3b to intact or total C3, or as a ratio of C3a to total C3.

"Complement-associated disorder," as used herein, refers to a disorder or condition characterized by a modification in complement activation. Examples of complement-associated disorders include, but are not limited to, trauma, such as traumatic brain injury, spinal cord injury, surgery, and intracranial pressure; inflammatory distress, such as severe allergies, systemic inflammatory response syndrome (SIRS), multiple organ failure (MOF), acute or adult respiratory distress syndrome (ARDS), septic shock, and shock; paroxysmal nocturnal hemoglobinuria (PNH); hereditary angiodema; renal disease, such as glomerular nephritis, infection, lupus nephritis, and renal disease requiring organ transplant; autoimmune disease, such as diabetes mellitus I, inflammatory bowel disease, Crohn's disease, multiple sclerosis, myasthenia gravis, rheumatoid arthritis, and systemic lupus erythematosus; ischemia/reperfusion injury; heart disease, such as myocardial infarction and cardiac arrest; pregnancy, including preeclampsia and fetal hypoxia syndrome; ocular disease, such as age-related macular degeneration, dry eye syndrome, and ocular infection; organ transplant, including transplant rejection, detecting imminent rejection, detecting infection, and monitoring adjustments in immunosuppressive drug regimens; infection, including sepsis, pneumonia, bladder infection, urinary tract infection, and kidney infection; and neurological disorders, including multiple sclerosis, Alzheimer's disease, Parkinson's disease, schizophrenia, and post-traumatic stress disorder.

"Control" refers to a sample having a known reference level of complement activation. In some embodiments, the control has a complement activation level comparable to that of an individual who is not experiencing a complement-associated disorder, such that a test sample having a complement activation level that is deviated compared to the control is indicative of a complement-associated disorder. In certain embodiments, a complement-associated disorder is indicated when the test sample complement activation level is statistically significantly deviated compared to the control.

"C3 activation signature," as used herein, means changes in C3 activation levels over time.

"Deviated" and "a deviation" as used herein, refer to statistically significant deviations as compared to a reference level in a control. Depending on the analyte being assayed, a deviated test sample level may be elevated or decreased relative to the control level.

"Decreased," as compared to a reference level in a control, means statistically significantly decreased. In an acute inflammatory response, intact C3 levels are depleted as C3 is broken down into its activation products. In certain embodiments, intact C3 levels are considered decreased as compared to a reference level in a control at about 10%.

"Elevated," as compared to a reference level in a control, means statistically significantly elevated. In an acute inflammatory response, iC3b levels increase as C3 is broken down into its activation products. In certain embodiments, a ratio of iC3b to intact C3 that is elevated as compared to the normal ratio of 0.005 is indicative of C3 activation.

"Epitope" refers to the minimum portion of a molecule that is recognized by, and thus determines the immunospecificity of, an antibody that binds to such epitope. The term is also used herein to refer to the minimum portion of a molecule that is recognized by a non-antibody specific binding agent. Unless otherwise indicated, it is assumed herein that a specific binding agent that binds to a complement protein binds to an epitope present and accessible for binding in the native protein, i.e., the epitope is not a neoepitope.

"Inflammatory distress" or "inflammatory dysfunction" occurs when the inflammatory response fails to resolve or remove the stimuli toward which the inflammatory response is directed. In such acute cases, the inflammatory response increases until homeostatic control over the process erodes. In one embodiment, a complement activation level determined by the assays and methods disclosed herein correlates directly with the severity of inflammatory distress being experienced by an individual. For example, when iC3b concentration is about 1-2.5% of intact C3, the patient's inflammatory distress can be said to be mildly severe. When iC3b concentration is about 2.5-5% of intact C3, the patient's inflammatory distress can be said to be moderately severe. When iC3b concentration is over 5% of intact C3, the patient's inflammatory distress is said to be highly severe. Understanding the severity of a patient's inflammatory distress can inform a physician's treatment of the individual. For example, if the individual presents with a highly severe inflammatory distress level, as indicated by the assays and methods disclosed herein, the physician can provide emergency medical treatment within the earliest time points of inflammatory distress, in order to minimize damage from inflammatory response.

"Label" refers to a moiety that facilitates the direct or indirect detection and/or quantitative or relative measurement of a molecule to which it is attached. A detectable label often produces a signal such as fluorescence, chemiluminescence, radioactivity, color, magnetic or paramagnetic properties, etc., that renders it detectable, e.g., by the use of instruments that detect fluorescence, chemiluminescence, radioactivity, color, magnetic field, magnetic resonance, etc., or in some cases by visual inspection. The label may be, e.g., fluorescent substance; pigment; chemiluminescent or luminescent substance; colored substance; magnetic substance; or a non-magnetic metal particle such as gold colloid. In a specific embodiment, the detecting antibodies suitable for use in the instant methods and assays are conjugated to a colloidal gold label, which provides a color signal.

"Neoepitope" refers to an epitope that is generated or becomes detectable as a result of proteolytic cleavage of a complement component or cleavage product.

In certain embodiments of the assays and methods disclosed herein, the complement present in the body fluid sample tested is not substantially activated by the assay or method itself. "Not substantially activated," as used in this context, means that the lateral flow immunoassay results are substantially free of in vitro activation caused by the test methods and/or materials. In this way, false positive test results for complement activation are avoided, since the lateral flow immunoassay is rapid and requires less sample manipulation, thus avoiding many of the stimuli that contribute to in vitro complement activation.

"Point-of-care," as used herein, refers to a device or method that can be used or carried out at the bedside or site of injury of the patient. Point-of-care tests generally do not require shipping a sample to a laboratory for processing or the expertise of a skilled laboratory technician. The point-of-care methods and tests described herein allow a clinician to receive critical information at the patient's bedside, or at the site of traumatic injury or triage, which can direct patient care during the critical first moments after a physiological crisis that triggers complement activation.

"Reader" refers to an instrument suitable for the detecting of the signal produced by the label. Various instruments are known in the art for the detection of label signals in diagnostic testing. In a specific embodiment of the present invention, the label is colloidal gold and the reader is an instrument suitable for the qualitative and/or quantitative detection of the color signal produced by the label. Suitable readers are available commercially from a variety of vendors, including BioAssay Works (Ijamsville, Md.), the ESE-Quant from Qiagen (Hilden, Germany), Easterline LRE (Nordlingen, Germany), and Detekt Biomedical (Austin, Tex.). In a specific embodiment, the reader is a handheld reader that quantifies the amount or concentration of intact C3, iC3b, or total C3.

"Treatment," as used herein, encompasses any diagnostic, therapeutic, preventive, or remedial treatment administered to an individual. In some embodiments, treatment encompasses performing additional diagnostic testing on the individual. In other embodiments, treatment encompasses therapeutic treatment, such as a administering a therapeutic agent to the individual. In certain embodiments, the therapeutic agent is selected from the group consisting of antibiotics, anti-inflammatory agents, and inhibitors of complement. In other embodiments, treatment encompasses modifying a treatment the individual has already received or is receiving. For example, in one embodiment treating an individual on a ventilator encompasses optimizing the ventilator.

Overview of the Complement System

Figure 2:
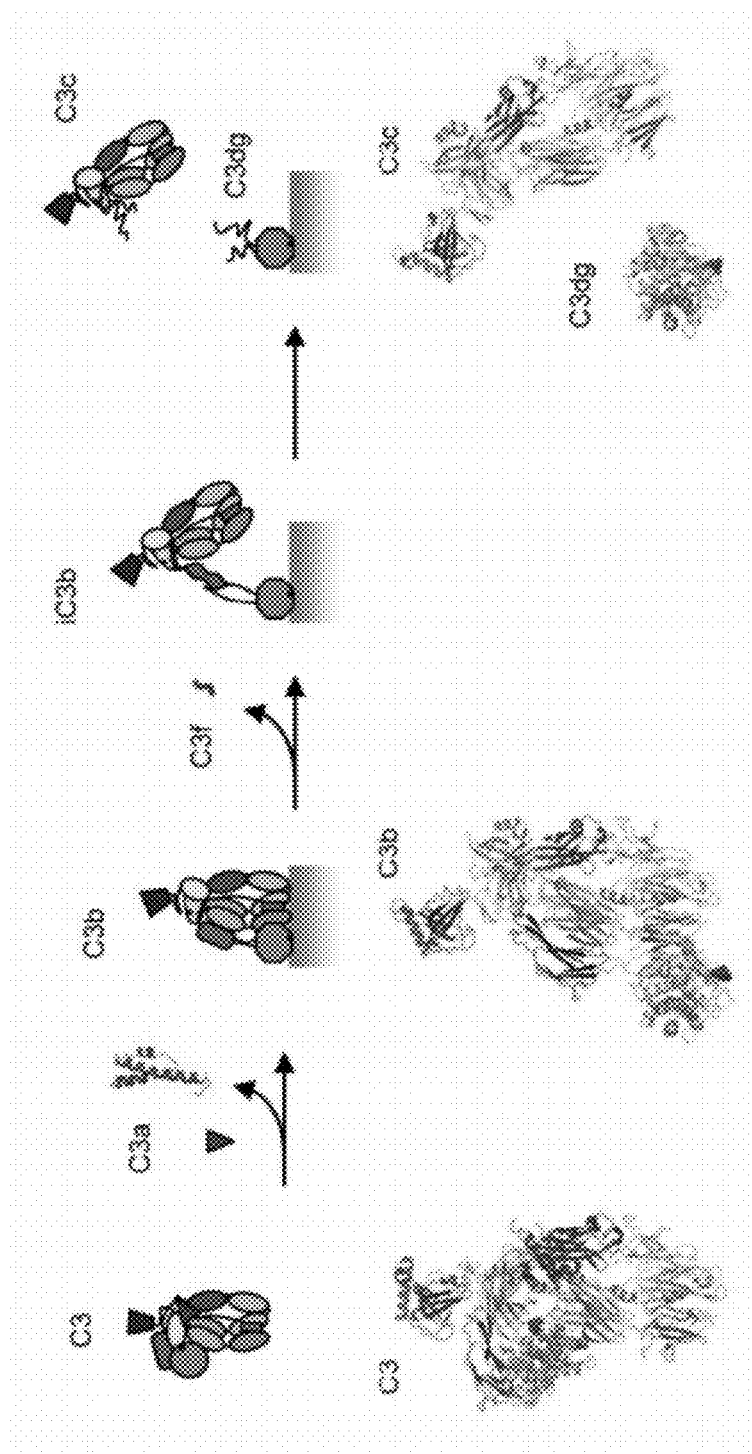
FIG. 2 provides a schematic representation of C3 activation and deactivation. Intact C3 is activated proteolytically to C3a and C3b. Some C3b molecules covalently attach to surfaces; others react with water and stay in circulation. C3b is deactivated by the protease Factor 1. The first deactivation product is iC3b, which is formed by the activity of Factor 1 removing a short peptide, C3f. iC3b is further degraded to C3c and C3dg, the latter ultimately being degraded to C3d.

The complement system comprises more than 30 serum and cellular proteins and plays important roles in innate and adaptive immunity. There are three major pathways of complement activation. The classical pathway is primarily activated by immune complexes, specifically IgG/IgM antibodies bound to antigen. Other activators include lipopolysaccharide, myelin, polyanionic compounds, C-reactive protein (CRP), and microbial DNA and RNA. The lectin pathway is activated by polysaccharides with free-mannose group and other sugars common to fungi and bacteria. The alternative pathway is mediated by direct C3 activation by "foreign" substances that often include microbial cell wall components. All three major pathways of complement activation converge on the central protein complement component 3 (C3). C3 is a central mediator of inflammation and is activated by most factors that cause inflammation. See FIGS. 1 and 2 for a schematic overview of the complement system.

The classical pathway is typically triggered by immune complexes, which are complexes of antigen bound with antibodies, generally belonging to the IgM or IgG isotypes. Immune complexes in turn bind to complement component C1, which is comprised of C1q, C1r, and C1s. The binding of C1q to an antibody-antigen complex triggers activation of C1r and C1s. Activated C1s then cleaves component C4 to produce C4a and C4b. C4b is capable of covalent attachment to cell surfaces, although only about five percent does so. The remaining 95 percent reacts with water to form a soluble, activated C4b. Component 2 can then associate with C4b, which after which it is activated by C1s to C2a and C2b. C4b and C2a combine to form C4bC2a, the classical pathway (CP) C3 convertase.

The CP convertase cleaves C3 to form C3a and C3b. Like activated C4b, C3b can covalently bind to cell surfaces or react with $H_2O$ and stay in solution. Activated C3b has multiple roles. By itself, it can serve as an opsonin to make the decorated cell or particle more easily ingested by phagocytes. In addition, C3b can associate with C4bC2a (the CP C3 convertase) to for a C5 convertase. The complex, termed C4bC2aC3b is termed the CP C5 convertase. Alternatively, C3b can form the core of another C3 convertase called the alternative pathway (AP) C3 convertase.

The alternative pathway (AP) is another mechanism by which C3 can become activated. It is typically activated by targets such as microbial surfaces and various complex polysaccharides and other materials. This alternative pathway can also be initiated spontaneously by the cleavage of the thioester bond in C3 by a water molecule to form $C3(H_2O)$. $C3(H_2O)$ binds factor B, which allows factor D to cleave factor B to Ba and Bb. Bb remains associated with $C3(H_2O)$ to form $C3(H_2O)Bb$ complex, which acts as a C3 convertase and cleaves C3, resulting in C3a and C3b.

C3b formed either via this process or via the classical or lectin pathways binds to targets (e.g., on cell surfaces) and forms a complex with factor B, which is subsequently cleaved by factor D and form Bb, resulting in C3bBb, which is termed the alternative pathway (AP) C3 convertase. Binding of another molecule of C3b to the AP C3 convertase produces C3bBbC3b, which is the AP C5 convertase.

The lectin complement pathway is initiated by binding of mannose-binding lectin (MBL) and MBL-associated serine protease (MASP) to carbohydrates. The MB1-1 gene (known as LMAN-1 in humans) encodes a type 1 integral membrane protein localized in the intermediate region between the endoplasmic reticulum and the Golgi. The MBL-2 gene encodes the soluble mannose-binding protein found in serum. In the human lectin pathway, MASp-1 and MASP-2 are involved in proteolysis of C4 and C2, leading to C3 convertase, which lead to production of a C5 convertase as described above for the CP.

C5 convertase generated via any of the three pathways cleave C5 to produce C5a and C5b. C5b then binds to C6, C7, and C8, which catalyses polymerization of C9 to form the C5b-9 membrane attack complex (MAC). The assembling MAC inserts itself into target cell membrane, forming a pore delineated by a ring of C9 molecules. MAC formation causes cell lysis of invading microbes, MAC formation on host cells can also cause lysis, but not necessarily. Sublytic amounts of MAC on the membrane of cells may affect cell function in a variety of way. The small cleavage products C3a, C4a, and C5a are anaphylatoxins and mediate multiple reactions in the acute inflammatory response. C3a and C5a are also potent chemotactic factors that attract immune system cells such as neutrophils and macrophages into the area of crisis.

Complement as a Biomarker for Physiological Crisis

Complement component C3 is useful as a general alert biomarker that the body is responding to some form of physiological crisis, such as injury, infection, or other disease process. Complement has been associated with a wide variety of diseases, including lupus, arthritis, intracranial hemorrhage, diabetes, multiple sclerosis, heart disease, and age-related macular degeneration. In many cases, the severity of disease correlates with the level of complement activation. In some cases, complement can play a role in disease pathology. In these cases, the body is not able to successfully control the cause of inflammation, which goes from local to systemic. Complement activation can directly damage tissue or do so indirectly by over-activating cells and recruiting immune cells that in turn cause tissue destruction. Examples of over activation include anaphylactic shock, multiple organ failure (MOF), acute respiratory distress syndrome (ARDS), and systemic inflammatory response syndrome (SIRS).

Complement activation in the immediate and early post-trauma period has been well documented and occurs by several different mechanisms, likely involving all three major pathways. Release and activation of proteolytic enzymes may directly activate complement components. Tissue damage and disruption of the endothelial lining expose surfaces that lack the endogenous complement inhibiting molecules that normally protect host tissues. These surfaces are susceptible to deposition of C3b and alternative pathway activation. Complement activation is also triggered by reperfusion of tissues following post-traumatic ischemia.

Multiple lines of evidence suggest that complement activation is an important factor in many of the complications of severe trauma, contributing significantly to FR injury, ARDS, MODS, secondary CNS injury, and sepsis. First, it is clear that complement activation is a common occurrence in the immediate post-trauma period in human trauma victims, and several studies have provided evidence suggesting that the extent of complement activation correlates positively with poor outcomes. Second, there is considerable evidence that complement activation is a major cause of FR injury in animal models of trauma as well as in human trauma victims. Third, numerous studies have demonstrated that complement deficiency or administration of complement inhibitors reduces tissue damage and improves outcomes in a variety of experimental models including hemorrhage, FR injury, and CNS injury.

Several studies measured complement activation in trauma patients at sequential time points following severe trauma and investigated the existence of a correlation between complement activation and injury severity. Adverse outcomes such as ARDS, multi-organ failure, sepsis, and death were also monitored in relation to complement activation. In one study, complement parameters were determined over 14 days in trauma patients at risk of ARDS. All patients showed a decrease in serum levels of C3, C4, C5 and of the inhibitors C1-INH, complement factor H (CFH), and complement factor I (CFI) in the first 24 hours, indicating consumption by high levels of complement activation. See Catania et al., *Immunological consequences of trauma and shock*, Ann. Acad. Med. Singapore 28:120-32 (1999); Hecke, et al., *Circulating complement proteins in multiple trauma patients—correlation with injury severity, development of sepsis, and outcome*, Crit. Care Med. 25(12): 2015-24 (1997); Huber-Lang et al., *Complement-induced impairment of innate immunity during sepsis*, J. Immunol. 169:3223-31 (2002); Kang et al., *Change of complement system predicts the outcome of patients with severe thermal injury*, J. Burn Care Rehabil. 24:148-53 (2003); and Younger et al., *Detrimental effects of complement activation in hemorrhagic shock*, J. Appl. Physiol. 90:441-46 (2001).

Lateral Flow Assays for the Detection and Quantification of Complement Activation and their Methods of Use The presently disclosed assays and methods provide several advantages over previous complement assays and methods known in the art: First, the instant assays and methods are suitable for point-of-care use, producing results in a matter of minutes, rather than hours. The rapid return of results allows a clinician to act upon changes in C3 activation in near real-time to direct patient care during the critical first moments after traumatic injury or at the onset of physiologic crisis. The assays and methods are relatively easy to use and do not require the availability of an outside laboratory or a skilled lab technician. Second, the instant assays and methods require fewer handling steps, and thus minimize intact C3 activation due to handling and processing, which leads to false positive test results. Third, the assays and methods described herein employ antibody pairs carefully selected to allow for measurement of the complement proteins intact C3 and/or iC3b, C3's major activation biomarker. This more precise measurement of complement activation, in comparison to traditional assays of total C3, permits analysis of turnover and actual amount of C3 remaining and available for activation.

In one embodiment, a method for treating an individual at risk for a complement-associated disorder is provided, the method comprising: (a) obtaining a sample of a body fluid from the individual; (b) measuring a complement activation level in the sample via a point-of-care lateral flow immunoassay; (c) correlating the complement activation level in the sample to a risk of a complement-associated disorder by comparing the complement activation level in the sample to a reference level in a control, wherein a deviation in complement activation level in the sample compared to the reference level in the control indicates the individual is at risk for a complement-associated disorder; (d) selecting a treatment for the individual, based on the correlating of step (c); and (e) treating the individual with the treatment selected in accordance with step (d).

In another embodiment of the method, the complement-associated disorder is selected from the group consisting of trauma, inflammatory distress, autoimmune disorders, intracranial hemorrhage, infection, transplant rejection, ocular disease, heart disease, ischemia/reperfusion injury, age-related macular degeneration, paroxysmal noctural hemoglobinuria (PNH), hereditary angioedema, renal disease, pregnancy-associated disorders, and neurological disorders. In a specific embodiment, the complement-associated disorder is inflammatory distress. Inflammatory distress, also known as inflammatory dysfunction, includes a variety of diseases and conditions associated with hyperinflammation. Examples of diseases and conditions associated with inflammatory distress include, but are not limited to, organ failure, systemic inflammatory response syndrome (SIRS), adult respiratory distress syndrome (ARDS), sepsis, and pneumonia.

In one embodiment of the method, the body fluid obtained from the individual is selected from the group consisting of whole blood, serum, plasma, urine, tears, saliva, wound exudate, broncheoalveolar lavage fluid, and cerebrospinal fluid. See FIG. 19 for a non-limiting list of suitable body fluids. In a specific embodiment, the body fluid is obtained from the individual within one hour of a physiological event triggering complement activation. In another specific embodiment, the body fluid is whole blood.

In one embodiment of the method, the lateral flow immunoassay detects the presence or absence of one or more of intact C3 and iC3b in the sample. In another embodiment of the method, the lateral flow assay detects the presence of total C3. In another embodiment, the lateral flow immunoassay is read by a reader. In a more specific embodiment, the reader quantifies a concentration of one or more of intact C3 and iC3b in the sample. In another specific embodiment, the reader quantifies a concentration of total C3 in the sample.

Complement activation levels are assessed for deviation from a reference value of a control which indicates complement is activated in the individual. In certain embodiments, the level or concentration of iC3b in the test sample is elevated in comparison to a control, indicating C3 is activated and has been further split into its activation product, iC3b. In other embodiments, the level or concentration of intact C3 is decreased in comparison to a control, indicating intact C3 has been converted to its breakdown or activation products and is hence depleted in the individual.

Complement activation level correlates to a severity of inflammatory distress: the higher the complement activation level, the greater the risk of developing inflammatory distress and/or the greater the severity of inflammatory distress experienced by the individual. Therefore, in another embodiment of the method, the complement-associated disorder is inflammatory distress and the concentration of one or more of intact C3 and iC3b correlates to a severity of inflammatory distress.

The complement activation level determined by the instant method provides point-of-care diagnostic information that can direct patient care. Based on the risk of complement-associated disorder correlated in step (c), the clinician can select the appropriate treatment for the individual. In one embodiment, the treatment comprises performing additional testing on the individual to determine the cause of inflammatory distress. For example, severe trauma patients that require ventilator assistance for breathing are at risk for acute respiratory distress caused either by Ventilator Associated Pneumonia (VAP) or non-infectious inflammatory dysfunction. A level of complement activation may indicate active or imminent inflammatory dysfunction before clinical signs of respiratory crisis are presented. The instant assays and methods may indicate whether the individual is experiencing VAP or non-infectious respiratory distress. Alternatively, the instant assays and methods may indicate additional testing (such as broncheoalveolar lavage (BAL)) at a time point earlier than is now standard practice If the individual is suffering from VAP, the treatment may comprise administering a therapeutic agent such as an antibiotic or set of antibiotics. If the inflammatory dysfunction is caused by non-infectious means, a therapy may be selected from the group consisting of ventilator adjustment, anti-inflammatory agents, and inhibitors of complement.

If the individual is suffering from traumatic brain injury or intracranial hemorrhage, the additional testing may comprise obtaining a cerebrospinal fluid sample for additional analysis. If the individual is suffering from a wound, including a non-healing wound, the further testing may comprise obtaining a sample of wound exudate for additional analysis.

Many inhibitors of complement are known in the art and suitable for use in the instant methods. In one embodiment, the inhibitor of complement is selected from the group consisting of natural complement inhibitors and derivatives thereof, compstatin and analogs thereof, anti-membrane attack complex (MAC) antibodies, anti-C3 antibodies, anti-05 antibodies, C3a receptor antagonists, and C5a receptor antagonists. Examples of additional complement inhibitors can be found, for example, in Emlen et al., *Therapeutic complement inhibition: new developments, Semin. Thromb. Hemost.* 36(6):660-68 (2101); Wagner et al., *Therapeutic potential of complement modulation, Nat. Rev. Drug Discov.* 9(1):43-56 (21010); and Ricklin et al., *Complement-targeted therapeutics, Nat. Biotechnol.* 25(11):1265-75 (2007), the contents of which are incorporated by reference herein in their entirety.

One of the benefits of the instant method is the rapid return of results, which enables a clinician to direct patient care in response to changes in complement activation in near real-time. Whereas previous assays for complement activation known in the art require full laboratories, skilled technicians, and hours to complete, the instant methods and assays provide results in a much shorter time frame. In one embodiment, the instant method provides a measurement of the complement activation level in the sample in about 30 minutes or less. In a more specific embodiment, the method provides a complement activation level in the sample in about 30, about 25, about 20, about 15, about 10, about 5, or about 3 minutes or less. The rapidity of the method enables the clinician to determine a complement activation level and select an appropriate therapy in response, during a clinically-meaningful time period. Indeed, the instant methods can be carried out at the bedside or even at the site of traumatic injury—for example, in an ambulance or in triaging a patient on the battlefield—and the complement activation level determined by the assay and method can direct patient care within the critical first hour post-trauma.

In another aspect of the invention, a method is provided for monitoring an individual who has received or is receiving treatment for a physiological condition and who is known to be suffering from a complement-associated disorder, the method comprising: (a) obtaining serial samples of a body fluid from the individual; (b) determining a complement activation level in each of said samples via a point-of-care lateral flow immunoassay; (c) comparing the complement activation levels in the serial samples to detect a change in a complement activation level over time; and (d) modifying treatment for the individual, based on the correlating of step (c). Serial blood samples are collected and tested to monitor complement activation levels in response to the treatment.

In one embodiment, the complement-associated disorder is selected from the group consisting of systemic lupus erythematosus, inflammatory distress, autoimmune disorders, intracranial hemorrhage, bacteremia, transplant rejection, ocular disease, heart disease, ischemia/reperfusion injury, age-related macular degeneration, paroxysmal nocturnal hemoglobinuria (PNH), hereditary angiodema, renal disease, pregnancy-associated disorders, and neurological disorders, and trauma including patients at risk for inflammatory dysfunction such as ventilator associated pneumonia (VAP), respiratory distress, and multiple organ failure.

As with other methods disclosed herein, in certain embodiments, the body fluid is selected from the group consisting of whole blood, serum, plasma, urine, tears, saliva, wound exudate, broncheolar lavage fluid, and cerebrospinal fluid. In one embodiment, the lateral flow immunoassay detects the presence or absence of one or more of intact C3 and iC3b in the sample. In another embodiment, the lateral flow immunoassay is read by a reader which is capable of quantifying a concentration of intact C3, iC3b, or total C3.

In certain embodiments, the clinician will detect a decrease in complement activation in response to the treatment the patient is receiving. Accordingly, the clinician will modify the individual's treatment by adjusting the dosing of medications administered, such as anti-inflammatory agents or complement inhibitors, or discontinuing treatment once complement levels have returned to normal (i.e., a level in an individual who is not experiencing a complement-associated disorder). In other embodiments, the clinician will detect a rise in complement activation levels in response to the treatment the patient is receiving. Accordingly, the clinician will modify the individual's treatment by increasing the dosage of medications, such as anti-inflammatory agents or complement inhibitors, until a desired stabilization or decrease in complement activation levels is achieved. If no change in complement activation level is detected, the clinician may modify the individual's treatment or may elect to maintain the individual's treatment regimen until a change in complement activation levels is observed.

Figure 4:
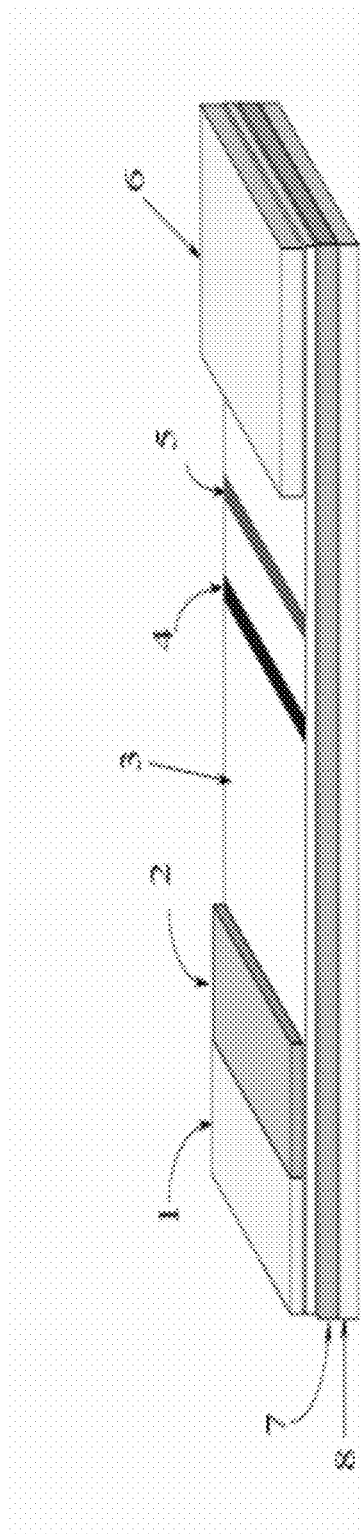
FIG. 4 is a schematic of one embodiment of a lateral flow immunoassay of the present invention.

Referring to FIG. 4, the lateral flow immunoassay described herein is comprised of a cellulose membrane strip 3, upon which is disposed a sample pad 1 to absorb the sample fluid and allow gradual migration of the sample-and-particle-conjugate immune complexes, a wick 6 at the distal end of the strip that absorbs the liquid sample and conjugate material to facilitate capillary migration through the cellulose membrane strip 3, and a particle conjugate pad 2 comprising a detecting antibody bound to a label, or detection conjugate. The cellulose membrane strip 3 is the test zone region, upon which is disposed a test line 4, comprising monoclonal or polyclonal antibodies striped for capturing the detection conjugate and a control line 5, comprising an antibody that binds a control analyte, such as IgG, and indicates to the user that the test was successfully run. The lateral flow immunoassay further comprises a polyester film backing 7 attached to the cellulose membrane strip 3, and a pressure-sensitive laminate film backing 8. Each lateral flow immunoassay is packaged in a Mylar® zero-vapor barrier pouch.

When a test sample is applied to the sample pad 1, the sample migrates from the sample pad 1 through the particle conjugate pad 2, where any target analyte present will bind to the detecting antibody conjugate. The sample then continues to migrate across the membrane 3 until it reaches the test line 4 where the target/conjugate complex will bind to the immobilized antibodies producing a visible line on the membrane. The sample then migrates further along the membrane strip 3 until it reaches the control line 5, where excess antibody conjugate that did not bind the test line will bind the control line and produce a second visible line on the membrane. The control line ligand is often an antibody against the Fc region of the conjugated antibody. This control line indicates that the sample has migrated across the membrane as intended.

Figure 5:
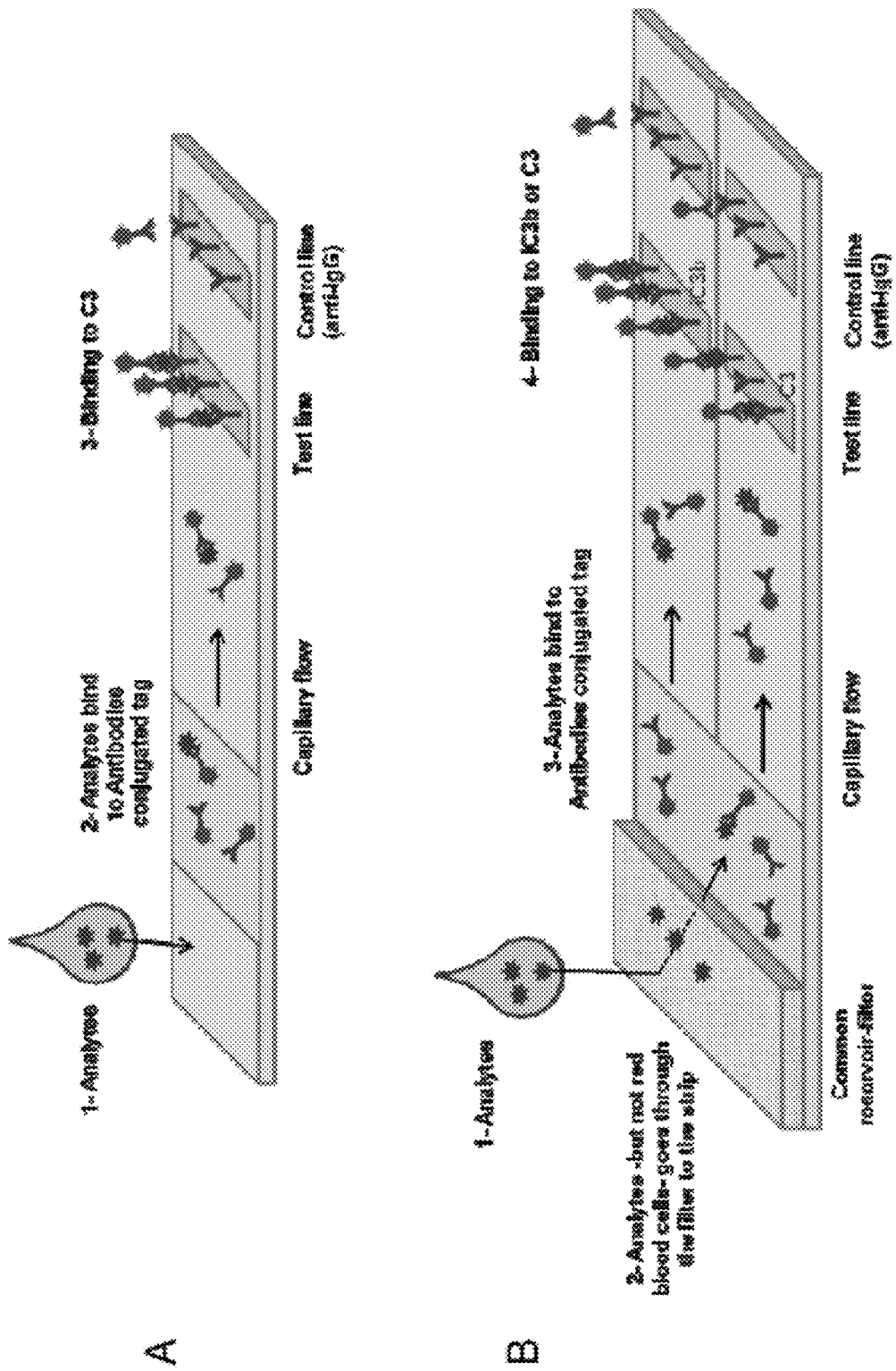
FIG. 5 is a schematic representation of two embodiments of a lateral flow immunoassay. (A) shows a lateral flow immunoassay for detection of a single analyte. (B) shows a lateral flow immunoassay for detection of two separate analytes (intact C3 and iC3b) in parallel membrane strips.
Figure 9:
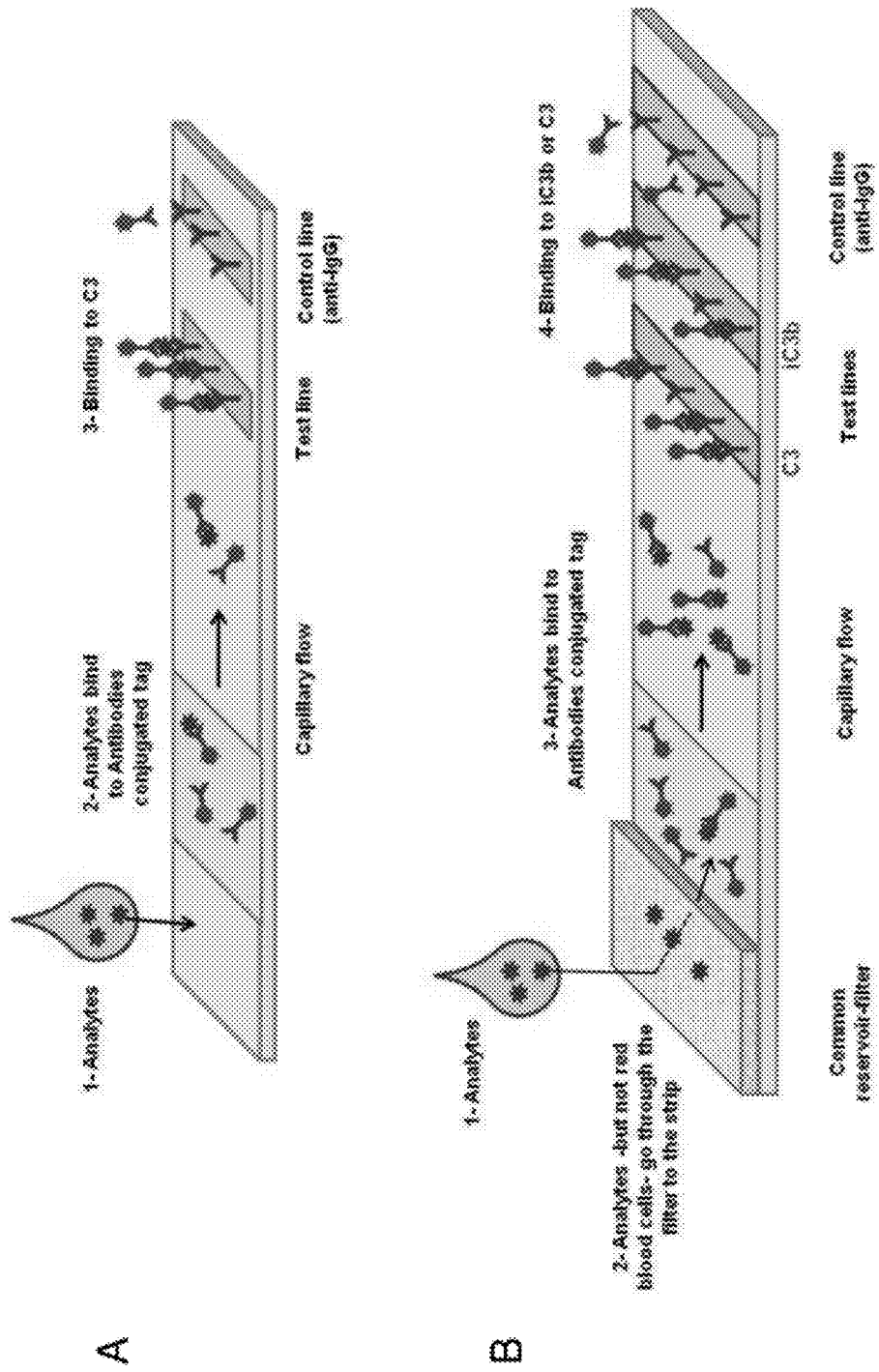
FIG. 9 is a schematic representation of two embodiments of a lateral flow immunoassay. (A) shows a lateral flow immunoassay for detection of a single analyte. (B) shows a lateral flow immunoassay for detection of two separate analytes (intact C3 and iC3b) in series on the same membrane strip.

In certain embodiments, the lateral flow immunoassay comprises a single membrane strip for the detection of a single analyte. In other embodiments, the lateral flow immunoassay detects two or more analytes. When the lateral flow immunoassay detects two or more analytes, the test can be configured with multiple membrane strips arranged in parallel (see, for example, the schematic of FIG. 5(B)), or with multiple test lines arranged in series on a single membrane strip (see, for example, the schematic of FIG. 9(B)).

Figure 6:
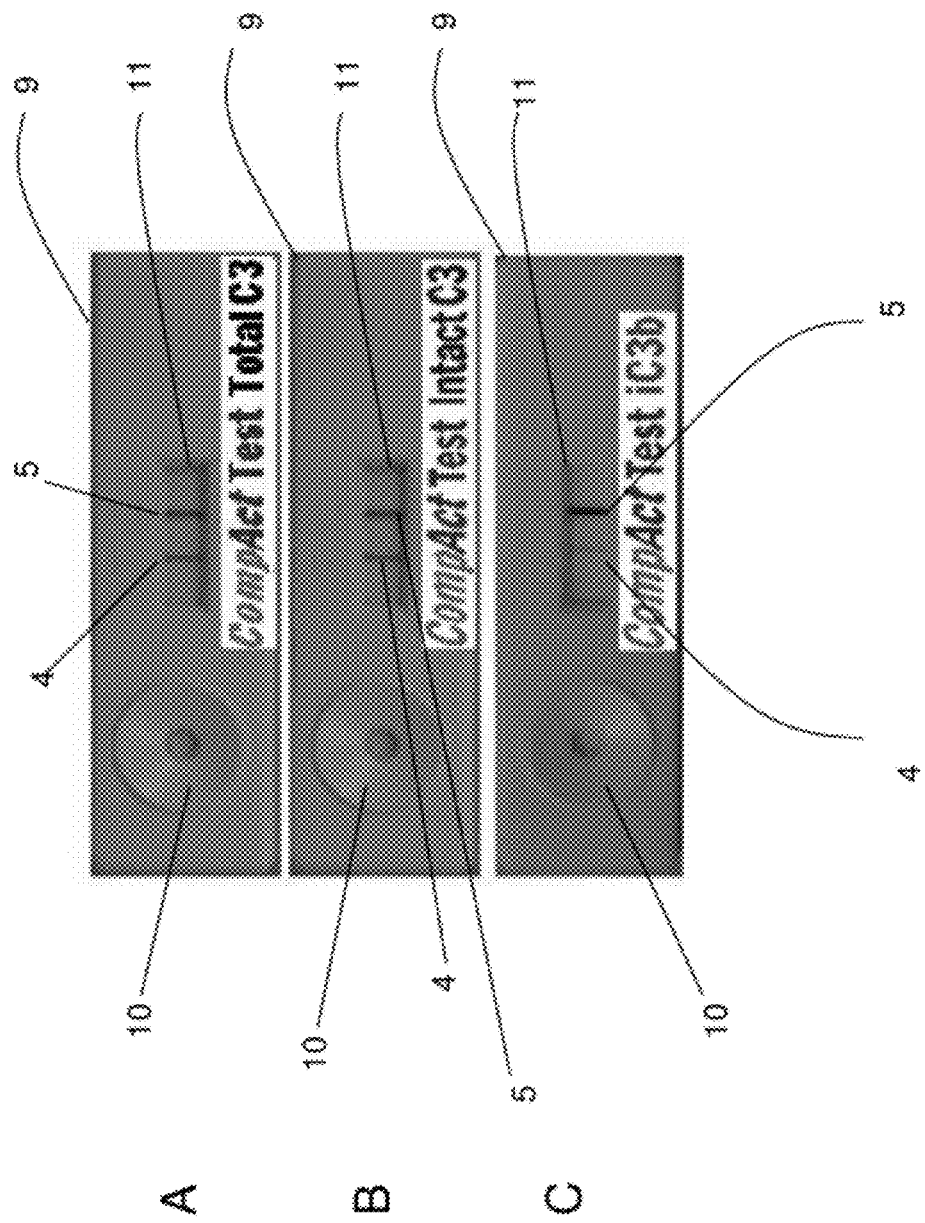
FIG. 6 is a depiction of three embodiments of single analyte lateral flow immunoassays. (A) shows a test cassette for a total C3 lateral flow immunoassay. (B) shows a test cassette for an intact C3 lateral flow immunoassay. (C) shows a test cassette for an iC3b lateral flow immunoassay.

Referring to FIG. 6, in some embodiments, the lateral flow immunoassay membrane strip is enclosed in a test, cassette 9 having a port 10 for instilling the test sample and a window 11 for viewing the test results. The lateral flow immunoassays of FIG. 6 are configured to assay for a single analyte and each comprise one test line 4 and one control line 5.

Figure 7:
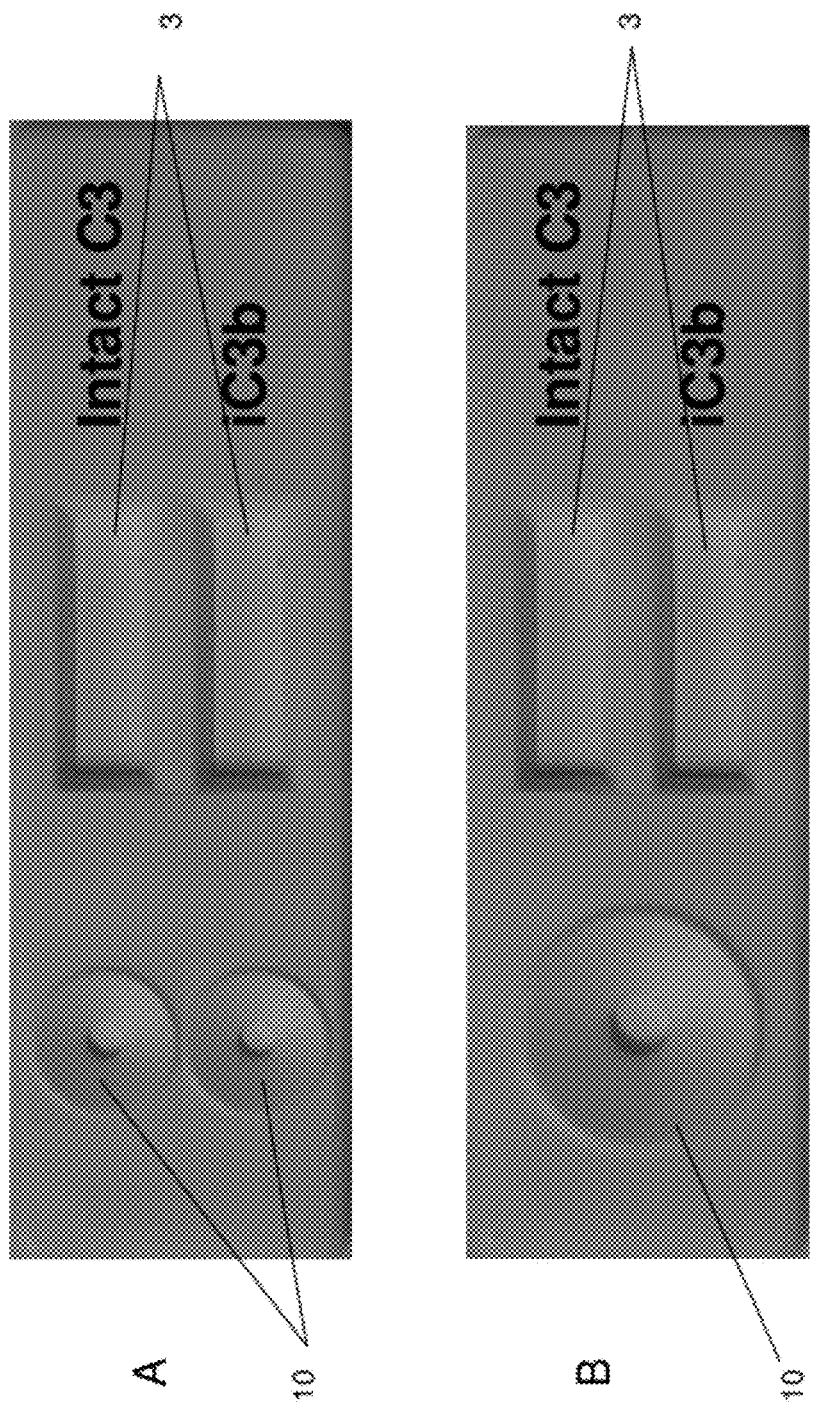
FIG. 7 is a depiction of two embodiments of a double analyte lateral flow immunoassay test cassette, for the assessment of intact C3 and iC3b. (A) shows a test cassette comprising two separate ports for sample loading and two membrane strips in parallel, one for each analyte. (B) shows a test cassette with a single port for sample loading and two membrane strips in parallel, one for each analyte.

Referring to FIG. 7, in some embodiments, the lateral flow immunoassay is configured to test for two analytes in a single test cassette in parallel. In some embodiments, the lateral flow immunoassay comprises two ports 10 for instilling the test samples and a separate membrane strip 3 for each analyte (see FIG. 7(A)). In other embodiments, the lateral flow immunoassay comprises one port 10 for instilling the sample and a separate membrane strip 3 for each analyte (see FIG. 7(B)).

Figure 8:
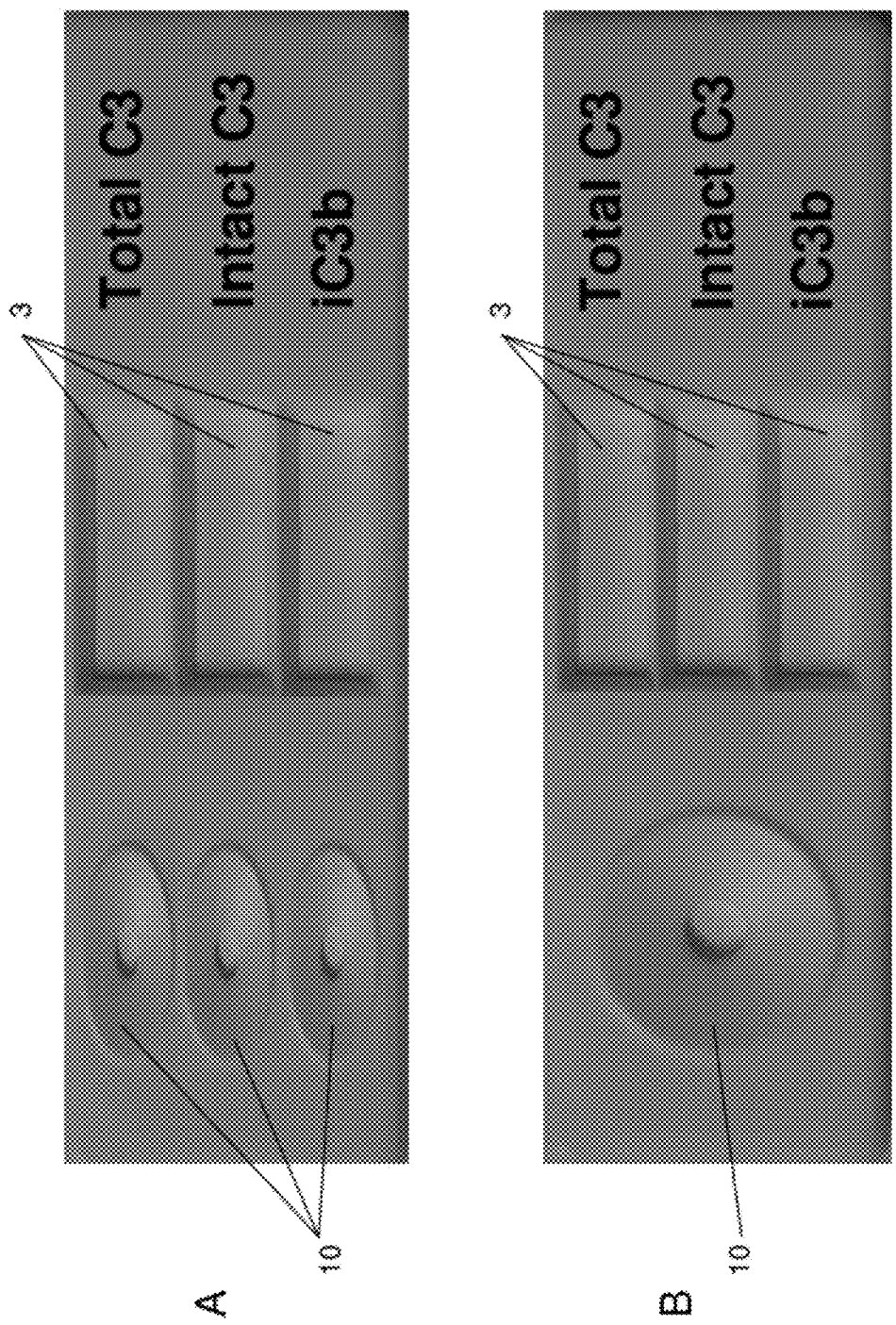
FIG. 8 is a depiction of two embodiments of a triple analyte lateral flow immunoassay test cassette, for the assessment of total C3, intact C3, and iC3b. (A) shows a test cassette comprising three separate ports for sample loading and three membrane strips in parallel, one for each analyte. (B) shows a test cassette with a single port for sample loading and three membrane strips in parallel, one for each analyte.

Referring to FIG. 8, in some embodiments, the lateral flow immunoassay is configured to test for three analytes in a single test cassette in parallel. In some embodiments, the lateral flow immunoassay comprises three ports 10 for instilling the test sample and a separate membrane strip 3 for each analyte (see FIG. 8(A)). In other embodiments, the lateral flow immunoassay comprises one port 10 for instilling the test sample and a separate membrane strip 3 for each analyte (see FIG. 8(B)).

Figure 10:
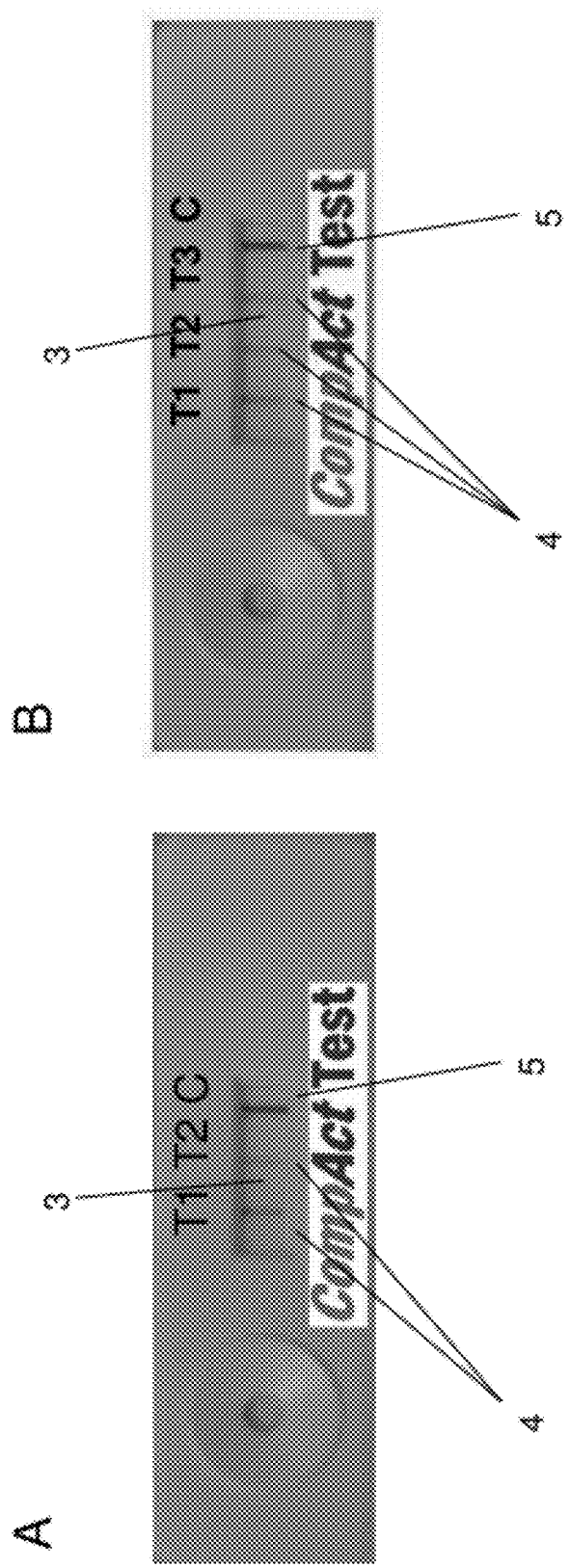
FIG. 10 is a depiction of two embodiments of a lateral flow immunoassay for multiple analytes in series. (A) shows a lateral flow immunoassay for detection of two analytes and a control in series on the same membrane strip. (B) shows a lateral flow immunoassay for detection of three analytes and a control in series on the same membrane strip. The analytes are selected from total C3, intact C3, and iC3b for both (A) and (B).

Referring to FIG. 10, in certain embodiments, the lateral flow immunoassay is configured to test for multiple analytes in a single test cassette in series. FIG. 10(A) depicts a test cassette comprising a membrane strip 3 with two test lines 4 and one control line 5 arranged in series. FIG. 10(B) depicts a test cassette comprising a membrane strip 3 with three test lines 4 and one control line 5 arranged in series.

The lateral flow immunoassay presently disclosed provides qualitative and/or quantitative detection of the target markers. Qualitatively, two clear lines on the membrane is a positive result, whereas a single line in the control zone is a negative result.

In one embodiment, a lateral flow immunoassay for the point-of-care detection of a marker of complement activation in a body fluid sample comprising complement proteins is provided, the lateral flow immunoassay comprising: a membrane strip; a detecting antibody that binds a first epitope of the marker; a test line comprising a capturing antibody that binds a second epitope of the marker; and a control line comprising an antibody that binds a control analyte, wherein the marker is selected from the group consisting of intact C3 and iC3b.

In one embodiment, the detecting antibody comprises a label that provides a signal that can be read visually by a clinician or electronically via a commercial reader. Various labels are suitable for use in the instantly disclosed assays. In a specific embodiment, the label is colloidal gold.

Detecting and capturing antibody pairs must be carefully selected to avoid interfering crosstalk between C3 and iC3b. The primary concern is intact C3 producing a signal in an assay for the detection of iC3b. As both molecules are derived from the same protein molecule, crosstalk can present a problem. As C3 is present at levels about 200 times higher than iC3b in normal individuals, even a slight degree of crosstalk can have a major impact on the accurate measurement of iC3b and C3 activation. This is further complicated by the fact that improper handling, improper storage, and even reagents themselves can cause in vitro C3 activation. Surprisingly, Applicants discovered that not all antibodies suitable for use in traditional ELISA assays are equally suitable for use in the assays of the instant invention. Tables 1 and 2 below show the difficulties in identifying antibody pairs suitable for use in the assays of the instant invention. The inventors analyzed 19 pairs of antibodies in the intact C3 immunoassay and 18 pairs of antibodies in the iC3b lateral flow immunoassay. Of these pairs, Hycult® HM2075 and MP Biomedicals® 55237 yielded the best results, with no cross-reactivity, in the intact C3 lateral flow immunoassay. Quidel® A209 with either MP Biomedicals® 55237 or Quidel® A250 yielded the best results in the iC3b lateral flow immunoassay. Interestingly, the inventors noted that antibody pairs suitable for use in traditional ELISA assays are not necessarily equally suitable for use in the lateral flow immunoassays described herein. For example, Hycult® HM2198 yielded an assay with about a 1% cross-reactivity, with considerable test-to-test variability. This cross-reactivity produced a false positive iC3b signal at a level of twice that of normal circulating iC3b. As actual double or tripling of iC3b levels would be signs of massive complement activation, a lateral flow immunoassay with 1% cross-reactivity is without clinical utility. MP Biomedicals® (55237) worked far better, producing cross-reactivity of less than about 0.5% (about 0.05%), compatible with clinical utility. However, it is noteworthy that both antibodies performed equally well in traditional ELISA assays.

TABLE 1

Antibody Screening Results in intact C3 assay

| capturing antibody | | | detection antibody | | | |
|---|---|---|---|---|---|---|
| species | antigen | supplier | species | antigen | supplier | notes |
| mouse | C3a | Hycult (HM2075) | goat | C3 | MP Biomedicals (55237) | no cross reactivity under assay conditions |
| mouse | C3a | Quidel (A203) | goat | C3 | MP Biomedicals (55237) | assay to assay variance too high |
| chicken | C3a | GenTex (GTX78198) | rabbit | C3d | Abcam (ab15981) | no positive readings (doesn't work) |
| mouse | C3a | Quidel (A203) | rabbit | C3d | Abcam (ab15981) | cross-reacts with C3b/iC3b +++ |
| goat | C3a | SantaCruz (sc17237) | rabbit | C3d | Abcam (ab15981) | the Ab may only react with C3a, not intact C3 |
| mouse | C3a | Hycult (HM2073) | rabbit | C3d | Abcam (ab15981) | cross reacts with C3b/iC3b + |
| mouse | C3a | Hycult (HM2074) | rabbit | C3d | Abcam (ab15981) | no positive readings |
| chicken | C3a | Abcam (ab48580) | rabbit | C3d | Abcam (ab15981) | no positive readings |
| mouse | C3a | Hycult (HM2073) | chicken | C3a | Abcam (ab48580) | no positive readings |
| mouse | C3a | Quidel (A203) | chicken | C3a | Abcam (ab48580) | no positive readings |
| chicken | C3a | Abcam (ab48580) | goat | C3 | MP Biomedicals (55237) | cross reacts with C3b/iC3b +++ |
| mouse | C3a | Hycult (HM2073) | goat | C3 | MP Biomedicals (55237) | cross reacts with C3b/iC3b +++ |
| goat | C3a | SantaCruz (sc17237) | goat | C3 | MP Biomedicals (55237) | similar to HM2073, better in diluted serum |
| rabbit | C3d | Abcam (ab15981) | mouse | C3a | Quidel (A203) | when anti-C3d is capture Ab, it binds to C3b and iC3b as well, which prevents efficient binding of intact C3 when analying mixed samples. |
| rabbit | C3d | Abcam (ab15981) | chicken | C3a | GenTex (GTX78198) | |
| rabbit | C3d | Abcam (ab15981) | goat | C3a | SantaCruz (sc17237) | |
| rabbit | C3d | Abcam (ab15981) | chicken | C3a | Abcam (ab48580) | |
| rabbit | C3d | Abcam (ab15981) | mouse | C3a | Hycult (HM2073) | |
| rabbit | C3d | Abcam (ab15981) | mouse | C3a | Hycult (HM2074) | |

TABLE 2

Antibody Screening Results in iC3b assay

| capturing antibody | | | detection antibody | | | |
|---|---|---|---|---|---|---|
| species | antigen | supplier | species | antigen | supplier | notes |
| mouse | iC3b | Quidel (A209) | goat | C3 | MP Biomedicals (55237) | no cross reactivity under assay conditions, good signal |
| mouse | iC3b | AbD serotec (MCA2607) | goat | C3 | MP Biomedicals (55237) | cross reacts with C3b/C3c at high conc. |
| mouse | iC3b | AbD serotec (MCA2607) | rabbit | C3d | Abcam (ab15981) | lower signal strength than using anti-C3 |
| mouse | iC3b | Quidel(A209) | rabbit | C3d | Abcam (ab15981) | lower signal strength than using anti-C3 |
| mouse | iC3b | Quidel(A209) | rat | C3d | Hycult (HM2198) | good signal, lower than using anti-C3 |
| mouse | iC3b | Quidel(A209) | rat | C3g | Hycult (HM 2199) | no signal |
| mouse | iC3b | Quidel(A209) | mouse | neo C3d | Quidel (A250) | lower signal strength than using HRP-anti C3, better specificity than using anti-C3d |
| rat | iC3b | Hycult (HM2199) | goat | C3 | MP Biomedicals (55237) | good signal |
| rat | iC3b | Hycult (HM2199) | mouse | active C3 | Hycult (HM2168) | weak signal |
| rat | iC3b | Hycult (HM2199) | mouse | active C3 | Hycult (HM2257) | no signal |
| rat | iC3b | Hycult (HM2199) | mouse | iC3b | Quidel (A209) | no signal |
| rat | iC3b | Hycult (HM2199) | mouse | neo C3d | Quidel (A250) | no signal |
| mouse | active C3 | Hycult (HM2168) | goat | C3 | MP Biomedicals (55237) | too much crosstalk with C3 |
| mouse | active C3 | Hycult (HM2168) | rat | C3g | Hycult (HM 2199) | weak signal |
| mouse | active C3 | Hycult (HM2257) | goat | C3 | MP Biomedicals (55237) | no signal |
| mouse | active C3 | Hycult (HM2257) | rat | C3g | Hycult (HM 2199) | no signal |
| mouse | C3 alpha | Meridian (H54189M) | goat | C3 | MP Biomedicals (55237) | no signal |
| mouse | neo C3d | Quidel (A250) | rat | C3g | Hycult (HM 2199) | very low signal |

Figure 3:
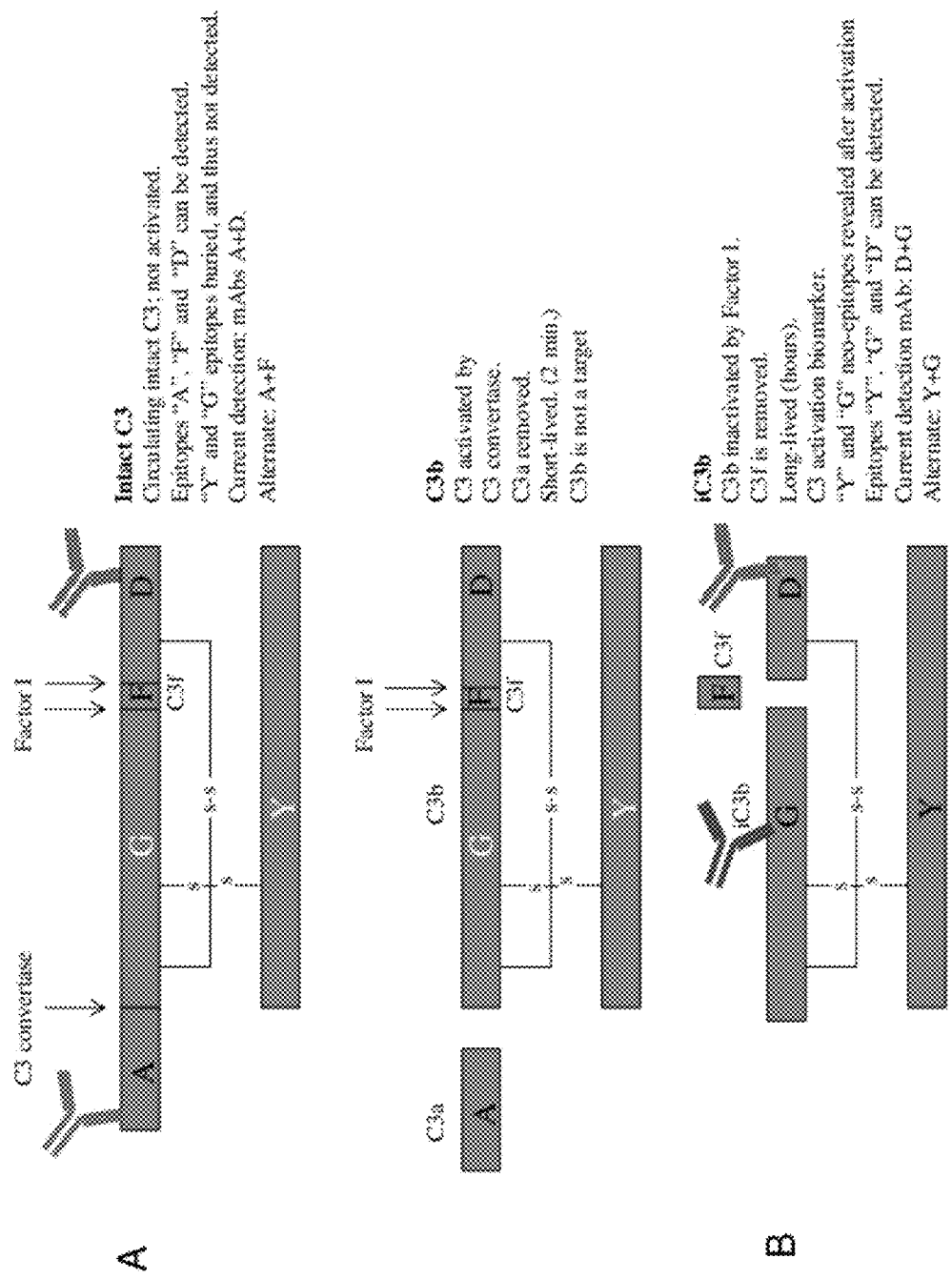
FIG. 3 is a schematic representation of specific recognition of intact C3 and iC3b by antibody pairs. (A) Intact C3 is recognized by two antibodies: a first antibody recognizes C3a, which is only present in the intact C3 molecule; a second antibody recognizes a region in C3d that is present in both intact C3 and iC3b. The second antibody participates in distinguishing C3 and its derivatives from other protein molecules but not intact C3 from iC3b. An alternate pair of antibodies for intact C3 include antibodies that recognized C3a and C3f. (B) The iC3b protein is recognized by another antibody pair. The first antibody contacts the protein at a neoepitope believed to be located near the C3g region. This epitope is revealed once Factor I removes the C3f fragment. The neoepitope is occluded once Factor I degrades iC3b to C3c and C3dg. The second antibody recognizes the C3d epitope. An alternate pair for iC3b includes the aforementioned iC3b antibody and a second that recognizes activated C3d (Quidel® A250).

In one embodiment, the marker is intact C3 and the detecting antibody binds a first epitope of intact C3, wherein the first epitope is a C3a domain which is present on intact C3 and which is lost upon activation of C3. In a further embodiment, the marker is intact C3 and the capturing antibody binds a second epitope on C3, wherein the second epitope is a region in the C3d domain which is present on intact C3, C3b, iC3b, and C3d. See FIG. 3(A).

In another embodiment, the marker is iC3b and the detecting antibody binds a first epitope of iC3b, wherein the first epitope is a neoepitope on iC3b which is revealed when C3b is deactivated to iC3b and which is occluded when iC3b is further degraded to C3c and C3d. In a further embodiment, the marker is iC3b and the capturing antibody binds a second epitope on iC3b, wherein the second epitope is a neoepitope present only on C3b, iC3b, and C3dg. See FIG. 3(B).

In a very specific example, the marker is intact C3, the capturing antibody is Hycult® HM2075 and the detecting antibody is MP Biomedicals® 55237. In another very specific example, the marker is iC3b, the capturing antibody is Quidel® A209 and the detecting antibody is MP Biomedicals® 55237. In another very specific example, the marker is iC3b, the capturing antibody is Quidel® A209 and the detecting antibody is Quidel® A250.

Various body fluids are suitable for use in the lateral flow immunoassays and methods of the instant invention. See, for example, FIG. 19, for a non-limiting list of suitable body fluids for use in the assays and methods described herein. In one embodiment, the body fluid is selected from the group consisting of whole blood, serum, plasma, urine, tears, saliva, wound exudate, bronchoalveolar lavage fluid, and cerebrospinal fluid. In a specific embodiment, the body fluid is whole blood.

One skilled in the art will appreciate that various control analytes are suitable for use in the lateral flow immunoassays of the instant invention to provide verification that the assay was successfully completed. In one embodiment, the control analyte is IgG.

Another advantage of the instant lateral flow immunoassay is the avoidance of substantial complement activation in the sample by virtue of the test itself, which can lead to false positive results. It is well known that C3 is a fastidious protein capable of self activation due to sample handling, storage, and contact with foreign materials or substances. Thus, the nature of C3 can lead to false positives in traditional ELISA and turbidity assays for complement activation that involve extensive sample handling and multiple steps. The instant lateral flow immunoassay avoids such false positives by reducing and/or eliminating sample preparation and handling steps. Accordingly, in one embodiment of the instant lateral flow assay, complement in the body fluid sample is not substantially activated experimentally by the lateral flow immunoassay.

In an alternative embodiment, it is desirable to have a lateral flow immunoassay that can detect more than one marker of complement activation in a single assay. For example, a dual lateral flow immunoassay that can qualitatively and quantitatively detect both intact C3 and iC3b in the same aliquot of a body fluid is highly desirable. Hence, in another embodiment, a lateral flow immunoassay for the point-of-care detection of markers of complement activation in a body fluid sample comprising complement proteins is provided, the lateral flow immunoassay comprising: a membrane strip; a first detecting antibody that binds a first epitope of intact C3; a first test line comprising a first capturing antibody that binds a second epitope of the intact C3; a second detecting antibody that binds a first epitope of iC3b; a second test line comprising a second capturing antibody that binds a second epitope of iC3b; and at least one control line comprising an antibody that binds a control analyte.

In one embodiment, the first and second detecting antibodies comprise a label that provides a signal. Various labels are suitable for use in the instantly disclosed assays. In one embodiment, the label is colloidal gold.

Various body fluids are suitable for use in the lateral flow immunoassays of the instant invention. See, for example, FIG. 19 for a non-limiting list of suitable body fluids. In one embodiment, the body fluid is selected from the group consisting of whole blood, serum, plasma, urine, tears, saliva, wound exudate, bronchoalveolar lavage fluid, and cerebrospinal fluid. In a specific embodiment, the body fluid is whole blood.

One skilled in the art will appreciate that various control analytes are suitable for use in the lateral flow immunoassays of the instant invention to provide verification that the assay was successfully completed. In one embodiment, the control analyte is IgG.

In another embodiment, complement in the body fluid sample is not substantially activated experimentally by the lateral flow immunoassay itself.

In one embodiment, the first detecting antibody binds a first epitope of intact C3, wherein the first epitope of intact C3 is a C3a domain which is present on intact C3 and which is lost upon activation of C3.

In another embodiment, the first capturing antibody binds a second epitope of intact C3, wherein the second epitope is a region in the C3d domain which is present on intact C3, C3b, iC3b, and C3d.

In another embodiment, the second detecting antibody binds a first epitope of iC3b, wherein the first epitope of iC3b is a neoepitope on iC3b which is revealed when C3b is deactivated to iC3b and which is occluded when iC3b is further degraded to C3c and C3d.

In still another embodiment, the second capturing antibody binds a second epitope of iC3b, wherein the second epitope of iC3b is a neoepitope present only on C3b, iC3b, and C3dg.

In another embodiment, the antibodies that bind intact C3 and the antibodies that bind iC3b are not substantially cross-reactive.

EXAMPLES

The following examples are given by way of illustration and are in no way intended to limit the scope of the present invention.

Example 1

Patient Triage

Before the first test sample is assayed, a standard curve is performed using 10 ng/ml 30 ng/ml, 100 ng/ml, 300 ng/ml, and 1000 ng/ml of intact C3 and iC3b standards. Lateral flow immunoassay cassettes are read with an electronic reader after 20 minutes.

The test is used to gauge injury severity within 15, 30, or 60 minutes of injury. It is most useful for patients who may have suffered injuries not obvious by visual inspection. A drop of blood is collected either from an arterial line (A-line) or finger stick. A 10 ul sample is drawn up using a fixed volume pipet. The sample then mixed with 990 ul of sample buffer. The blood and sample buffer are mixed. Using a fixed volume pipet bulb, 100 ul is drawn up and pipetted onto the lateral flow immunoassay cassette containing integrated intact C3 and iC3b test strips. Alternatively, 100 ul can be applied to separate intact C3 and iC3b lateral flow assay cassettes. After 10 minutes but before 40 minutes, the cassette is read and results recorded, preferably electronically by a reader. If the first reading has an iC3b level (or equivalent iC3b:intact C3 ratio) higher than 50 μg/ml in blood, evidence of complement activation and high inflammation exist. Staff assumes severe injury and alerts ER staff. Otherwise, a second reading is taken 5 minutes later. If the iC3b level (or equivalent iC3b:intact C3 ratio) is higher than 50 μg/ml in blood or the iC3b level has increased by more than 25%, the patient is assumed to have severe injury and ER staff is alerted. A lesser increase or no increase is suggestive, but not conclusive, of less severe injury.

Example 2

Trajectory Monitoring of a Trauma Patient

At the beginning of the shift, ICU staff performs a standard curve using 10 ng/ml 30 ng/ml, 100 ng/ml, 300 ng/ml, and 1000 ng/ml of intact C3 and iC3b standards. Lateral flow immunoassay cassettes are read with an electronic reader after 20 minutes.

The objective of trajectory monitoring is to detect changes in inflammatory and immune status of patients that have been stabilized after severe trauma. In this example, respiratory distress caused by either pneumonia or inflammatory dysfunction is to be detected. The expected patient profile is one who has an injury severity score (ISS) equal or greater to 16 and who requires ventilator assistance for breathing.

The patient receives a complement test at frequent intervals, which aligns with the time points for testing glucose levels in blood. This interval between testing is usually about two hours. Blood is collected using the same method as for glucose testing, either by A-line or by finger stick. A 10 ul sample is drawn up using a fixed volume pipet. The sample then mixed with 990 ul of sample buffer. The blood and sample buffer are mixed. Using a fixed volume pipet bulb, 100 ul is drawn up and pipetted onto the LFA cassette containing integrated intact C3 and iC3b lateral flow immunoassay cassettes. Alternatively, 100 ul can be applied to separate intact C3 and iC3b cassettes. The cassette or cassettes will be placed in reader at the patient's bedside. The reader is set to take a reading after 20 minutes. Data is collected and iC3b, intact C3 and iC3b:(intact C3) values recorded at each time point.

Changes in intact C3 or iC3b levels over time or changes in the rate of change may indicate a change in inflammatory status. A sharp rise in iC3b, accompanied by a decrease in intact C3, indicates imminent respiratory distress. As a next course of action, a clinician performs a broncheoalveolar lavage (BAL) on the patient to determine whether the patient is experiencing VAP. If bacteria are present at levels of $10^4$ per ml or higher, VAP is indicate and the patient is places on antibiotic therapy. Otherwise, noninfectious inflammatory dysfunction is assumed and the patient may be treated with anti-inflammatory agents and/or complement inhibitors. The patient may also have his ventilator setting adjusted.

Example 3

Determining Disease Severity and Effectiveness of Treatment in a Patient with Systemic Lupus Erythematosus (SLE)

Before the first test sample is assayed, a standard curve is performed using 10 ng/ml 30 ng/ml, 100 ng/ml, 300 ng/ml, and 1000 ng/ml of intact C3 and iC3b standards. Lateral flow immunoassay cassettes are read with an electronic reader after 20 minutes.

The test is used to gauge the initial severity of disease as well the effectiveness of therapy. One of the standard diagnostics performed on SLE patients is measurement of total C3 levels. C3 levels are normally depressed in SLE patients and return to normal (>1 mg/ml) following successful treatment. However, it not known generally whether the C3 activation has been abrogated or only slowed enough to allow normal replenishment mechanisms to restore C3 levels to normal.

At each doctor visit, a patient's blood is collected for total C3, intact C3, and iC3b tests. Only one drop is required for the combine 3 tests. Blood is collected by fingerstick unless blood is being drawn for other tests, in which case, the blood will come from that source. A 10 ul sample is drawn up using a fixed volume pipet. The sample then mixed with 990 ul of sample buffer. The blood and sample buffer are mixed. Using a fixed volume pipet bulb, 100 ul is drawn up and pipetted onto the LFA cassette containing integrated lateral flow cassette that measures total C3, intact C3 and iC3b. Alternatively, 100 ul can be applied to separate cassettes for each assay. The cassette or cassettes are placed in reader at the doctor's office. The reader is set to take a reading after 20 minutes.

Data is collected at each doctor visit. At the initial visit, adding the iC3b and intact C3 tests provides the specialist with more information about the severity of the patient's condition than is now possible. New information becomes available at the time that the specialist would consider the patient's status stable. At this point, the iC3b and intact levels indicate the extent of remaining disease process. If iC3b levels, in particular, are above normal (generally >1%), the underlying disease process is still very active and the specialist may opt to further adjust therapy by increasing anti-inflammatory drug doses or adding additional medication.

Example 4

Determination of Basal Intact C3 and iC3b Levels in the Basal Tear Fluid of a Healthy Individual Over a 24 Hour Period Before the first test sample is assayed, a standard curve is performed using 10 ng/ml 30 ng/ml, 100 ng/ml, 300 ng/ml, 1000 ng/ml, and 3000 ng/ml of intact C3 and iC3b standards. Lateral flow immunoassay cassettes are read with an electronic reader after 20 minutes.

For determining intact C3 and iC3b levels in the eye of a healthy individuals, three readings in total were taken. Samples were collected and evaluated of Time=0 hours, 12 hours, and 24 hours.

For tear collection, the lower eyelid is pulled back and briefly dapped with a Kimwipe® to the lower part of the eye. The Kimwipe® is then quickly cut where the tear was collected leaving a few millimeters of dry edge surrounding the tear spot. The Kimwipe®-tear sample is then placed into 220 ul of BioAssay Works Diluent Buffer and vortexed thoroughly for 10 seconds. After a one minute wait period, the sample is vortexed again briefly. Next, 100 ul of sample is transferred to each lateral flow immunoassay (intact C3 and iC3b) and assayed.

For analysis, each cassette is inserted into the reader and read after 20 minutes.

Figure 15:
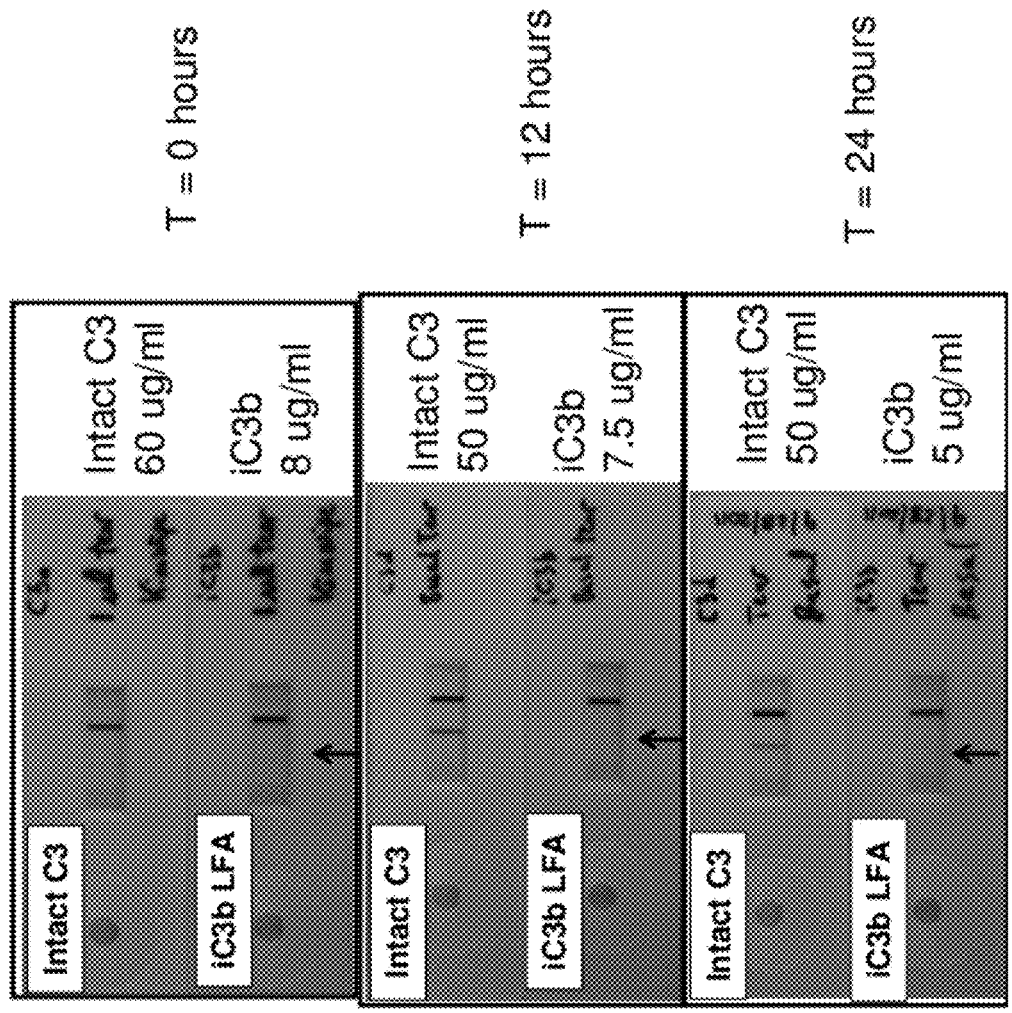
FIG. 15 shows intact C3 and iC3b levels in basal tears from a single individual at 12 hour intervals, as assayed by lateral flow immunoassays described herein.

The results ranged between 50-60 μ/ml of intact C3 and between 5-8 μ/ml of iC3b (See FIG. 15).

Example 5

Determination of Basal Intact C3 and iC3b Levels in Two Health Individuals at a Single Time Point Before the first test sample is assayed, a standard curve is performed using 10 ng/ml 30 ng/ml, 100 ng/ml, 300 ng/ml, 1000 ng/ml, and 3000 ng/ml of intact C3 and iC3b standards. Lateral flow immunoassay cassettes are read with an electronic reader after 20 minutes.

Resting levels of intact C3 and iC3b are collected from two healthy donors. The lateral flow immunoassay reader is turned on. Finger is cleaned using an alcohol swab. Finger is stuck with lancet and squeezed gently to collect 10 ul of blood using the MICROSAFE® Tube by capillary action. Blood sample was expelled directly into a tube filled with 990 ml of sample assay buffer and then capped and mixed by inversion 6-8 times. 100 ul of blood sample mixture was transferred to CompAct intact C3 test using the 100 ul Exact Volume Pipet. A second 100 ul of blood sample mixture was then transferred to the CompAct iC3b test using a fresh 100 ul Exact Volume Pipet. The timer was set to read after 20 minutes for both tests.

Figure 16:
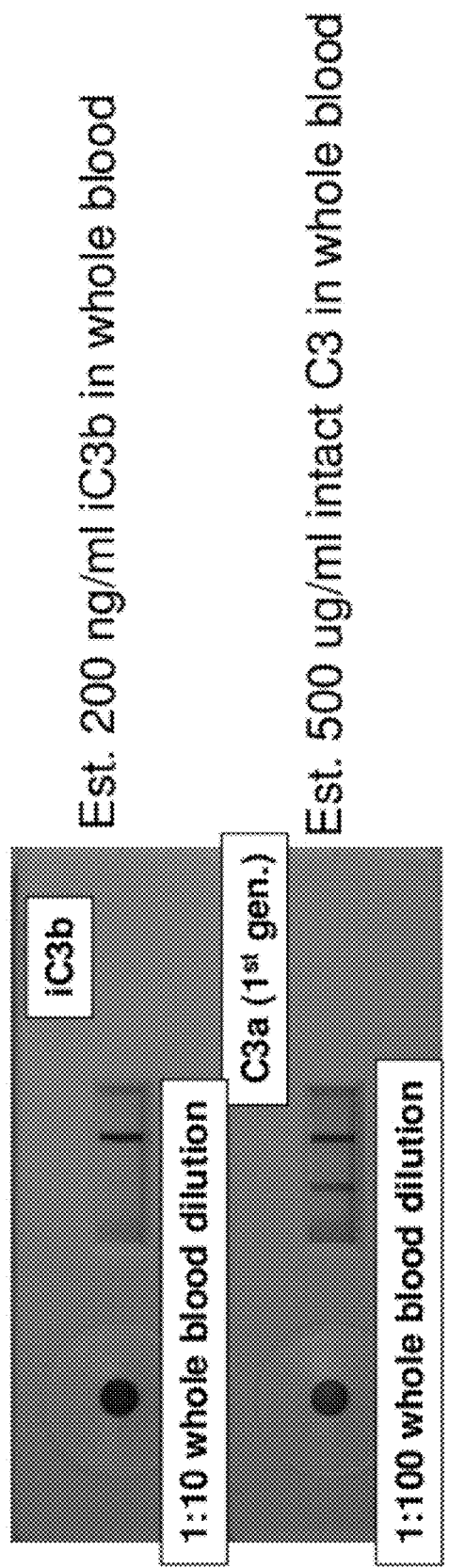
FIG. 16 shows intact C3 and iC3b levels in whole blood from a normal healthy individual. Results show approximately 2500-fold more intact C3 than iC3b in whole blood from a healthy donor.
Figure 17:
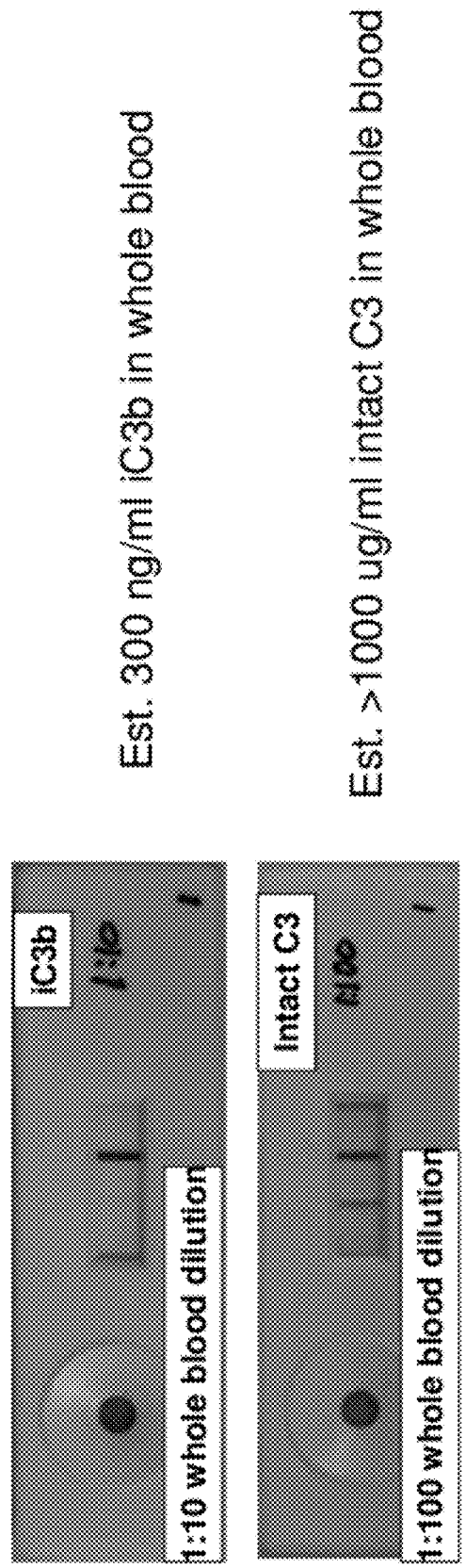
FIG. 17 shows intact C3 and iC3b levels in whole blood from a healthy individual. Results show approximately 333-fold more intact C3 than iC3b in whole blood from a healthy donor.

The results from the first patient were determined to be approximately 500 μg/ml for intact C3 and 200 ng/ml for iC3b. This indicates there is 2500 ratio of intact C3 to iC3b in this individual (see FIG. 16). The second individual's results were approximately 1000 μg/ml for intact C3 and 300 ng/ml for iC3b (see FIG. 17). Both of these values are within the expected normal ranges. The iC3b values are in the lower range of what is considered normal.

Example 6

Determination of Basal Intact C3 and iC3b Levels in a Healthy Individual at a Single Time Point after Strenuous Exercise Using the above protocol of Example 5, one of the healthy individuals was tested again after strenuous exercise (see FIG. 18). Exertion did not significantly alter iC3b or C3 levels.

Example 7

Crosstalk Between Intact C3 and iC3b Antibodies in Lateral Flow Immunoassays In a 1 milliliter volume, 50 ng/ml of iC3b was mixed with varying mounts of intact C3 (ranging from 0 ng/ml to 100,000 ng/ml). Samples were mixed by inversion 6-8 times and then 0.1 ml was pipetted onto the cassette. Readings were taken at 20 minutes. Reader output was converted to iC3b concentration using a standard curve generated from 10 ng/ml to 100,000 ng/ml. Background from a cassette run only with buffer was subtracted. Fractional contributions were calculated by subtracting the actual iC3b concentration (from iC3b test with no added C3) from apparent concentration of iC3b at each point and then normalizing against actual iC3b concentrations. See FIG. 14. For the H08K-01 cassettes, at the highest concentration of C3 tested, about half the iC3b signal came from intact C3 and half from actual iC3b. For the J24K-03 version, about four times as much iC3b signal came from intact C3 cross talk than from actual iC3b. Although these antibody pairs work well in ELISA assays, they exhibit significant crosstalk when used in lateral flow immunoassays for the same analytes. At the physiologically relevant 250:1 and 500:1 ratios, intact C3 contributes more to iC3b signal out put than iC3b itself in J24K-03.

J24K-03 is an assay with mouse anti-C3a monoclonal on the gold conjugate and mouse anti-C3d monoclonal on the test line. H08K-01 has mouse anti-iC3b monoclonal on the gold conjugate and Anti-C3 polyclonal on the test line.

Example 8

Generation of iC3b Standard Curve for Lateral Flow Immunoassays

Figure 11:
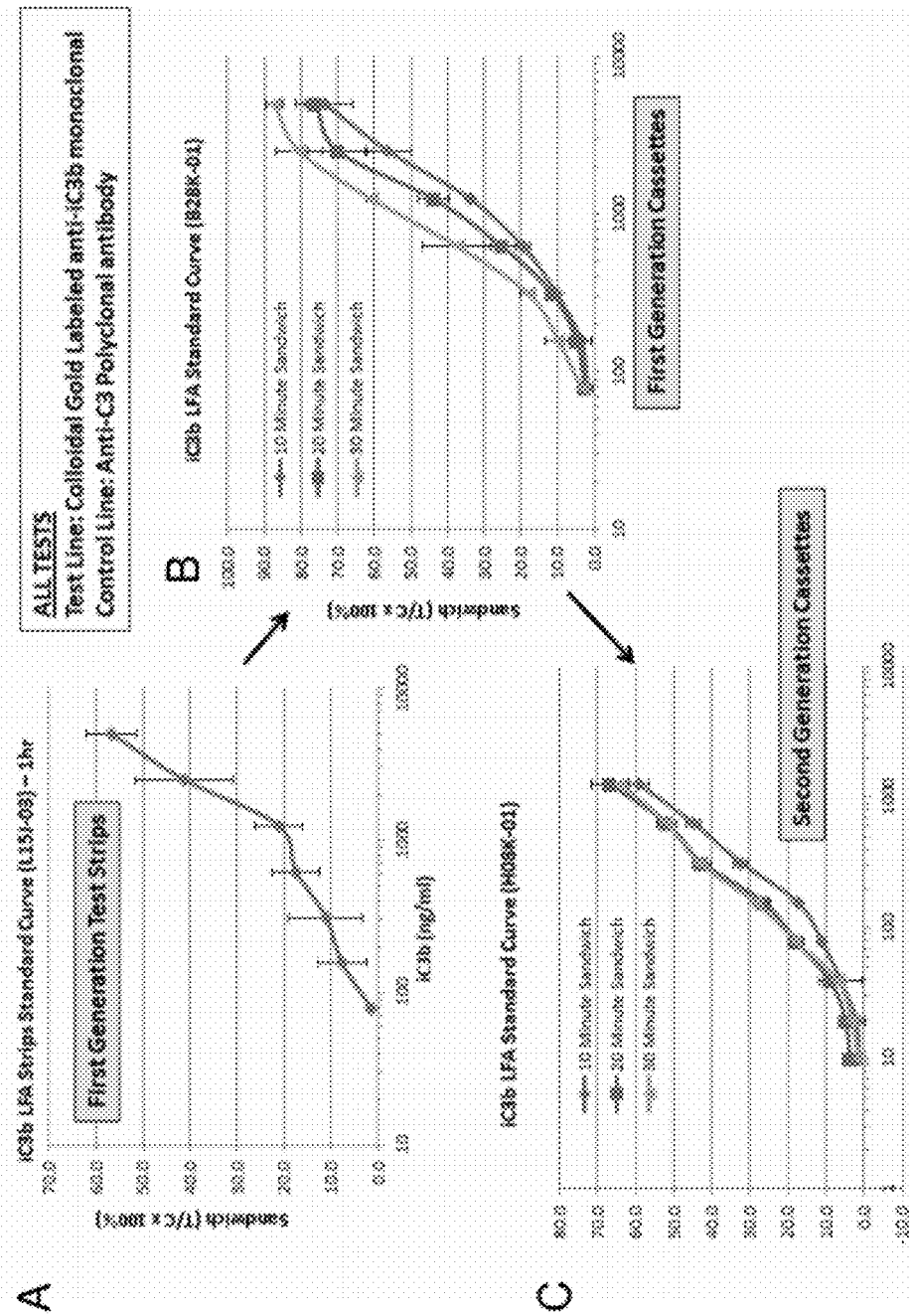
FIG. 11 shows a comparison of sensitivities, dynamic range, test-to-test variability, and assay time for three embodiments of the instant lateral flow immunoassays. (A) shows a standard curve graph of lateral flow for a test strip detecting iC3b without a cassette casing. (B) shows a standard curve graph of an embodiment of the lateral flow immunoassay wherein the test strips are enclosed in a cassette, which allows more controlled administration of the test sample volume. Concentration of antibody solution used for gold conjugation is 0.5 mg/ml and BSA is included in the reaction mixture. (C) shows a standard curve graph of another embodiment of a test strip integrated into a cassette, wherein the concentration of antibody solution used for gold conjugation is 1 mg/ml and BSA is removed from the reaction mixture. Sensitivity of the assay reaches 10 ng/ml with a dynamic range extending to 10 ug/ml.

One embodiment of the invention comprises a lateral flow assay strip without the cassette casings. These strips had anti-iC3b monoclonal (Quidel® A209) conjugated to the gold and anti-C3 antibody (MP Biomedical® 55237) conjugated to the strip. Standard curves are shown in FIG. 11(A). The standard curves indicated a linear range of about 10 fold and a sensitivity of about 100 ng/ml. Another embodiment of the invention configures the strips for use in a cassette that allows controlled application of the sample to the assay strip. This improved assay-to-assay reproducibility, although there is still considerable time dependence on the assay. Standard curve results are shown in FIG. 11(B). A third embodiment increases the antibody concentration from 0.5 mg/ml to 1 mg/ml applied to on the gold conjugate and removes BSA from the absorption buffer. Standard curve results are shown in FIG. 11(C).

Standard curves are generated as described in example 9 below.

Example 9

Generation of iC3b Standard Curve for Lateral Flow Immunoassays

Ten (10) μl of a stock of iC3b (concentration 1 mg/ml) was diluted into 990 ul of sample dilution buffer to create 10 ug/ml working stock using a 2 ml capped tube. Tube was mixed by slowly inverting 10-12 times. Investigator diluted 500 ul of 10 ug/ml stock into 500 ul BAW Buffer to create a 5 ug/ml stock in another 2 ml capped tube. Mixing was performed by slowly inverting tube 10-12 times. The 1:1 dilution (500 ul:500 ul) was repeated, as described above, nine more times to create the following working stocks:

10 ug/ml, 5 ug/ml, 2.5 ug/ml, 1.25 ug/ml, 625 ng/ml, 313 ng/ml, 156 ng/ml, 78 ng/ml, 39 ng/ml, 20 ng/ml, 10 ng/ml, and 0 ng/ml (buffer alone).

Lateral flow immunoassay (LFA) cassettes were prepared by labeling and laying out in groups of three. For each dilution, investigator pipetted 100 ul of first working stock (10 ug/ml for intact C3 and 5 ug/ml for iC3b) into sample port of 1st LFA. For each concentration, investigator waited 20 seconds before loading 100 ul of same working stock into the 2nd LFA. Cassettes were read after 10, 20, and 30 minutes using BioAssay Works Reader LFDR 101 (Forsite Diagnostics) using the Test line setting followed by the Control line setting, and the data recorded.

Figure 12:
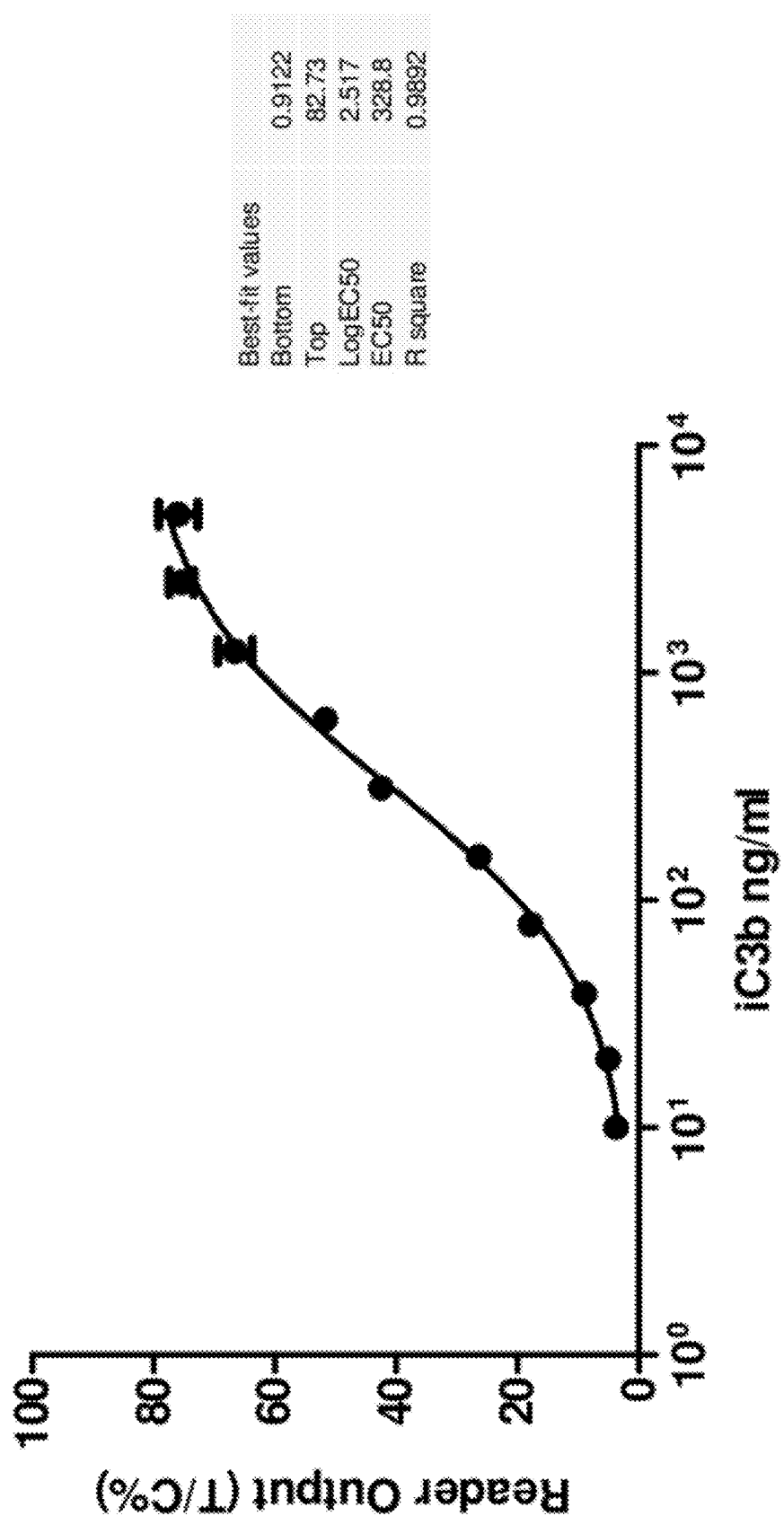
FIG. 12 shows sensitivity of a lateral flow immunoassay for iC3b described herein. Sensitivity ranges from 10 ng/ml to 10 ug/ml. Standard error is less than 3% at 20 minutes. R square=0.9892. Values were verified by ELISA.

After the experiment is completed, data was plotted using GraphPad Prism 5 software. The standard curve fits the three-parameter logistic equation: $Y=\text{Bottom} + (\text{Top} - \text{Bottom})/(1 + EC50/X)$. See FIG. 12.

Example 10

Generation of Intact C3 Standard Curve for Lateral Flow Immunoassays

Ten (10) μl of a stock of intact (concentration 1 mg/ml) was diluted into 990 ul of sample dilution buffer to create 10 ug/ml working stock using a 2 ml capped tube. Tube was mixed by slowly inverting 10-12 times. Investigator diluted 500 ul of 10 ug/ml stock into 500 ul BAW Buffer to create a 5 ug/ml stock in another 2 ml capped tube. Mixing was performed by slowly inverting tube 10-12 times. The 1:1 dilution (500 ul:500 ul) was repeated, as described above, nine more times to create the following working stocks:

10 ug/ml, 5 ug/ml, 2.5 ug/ml, 1.25 ug/ml, 625 ng/ml, 313 ng/ml, 156 ng/ml, 78 ng/ml, 39 ng/ml, 20 ng/ml, 10 ng/ml, and 0 ng/ml (buffer alone).

LFA cassettes were prepared by labeling and laying out in groups of three. For each of dilution, investigator pipetted 100 ul of first working stock (10 ug/ml for intact C3 and 5 ug/ml for iC3b) into sample port of 1st LFA. For each concentration, investigator waited 20 seconds before loading 100 ul of same working stock into the 2nd LFA. Cassettes were read after 10, 20, and 30 minutes using BioAssay Works Reader LFDR 101 (Forsite Diagnostics) using the Test line setting followed by the Control line setting, and the data recorded.

Figure 13:
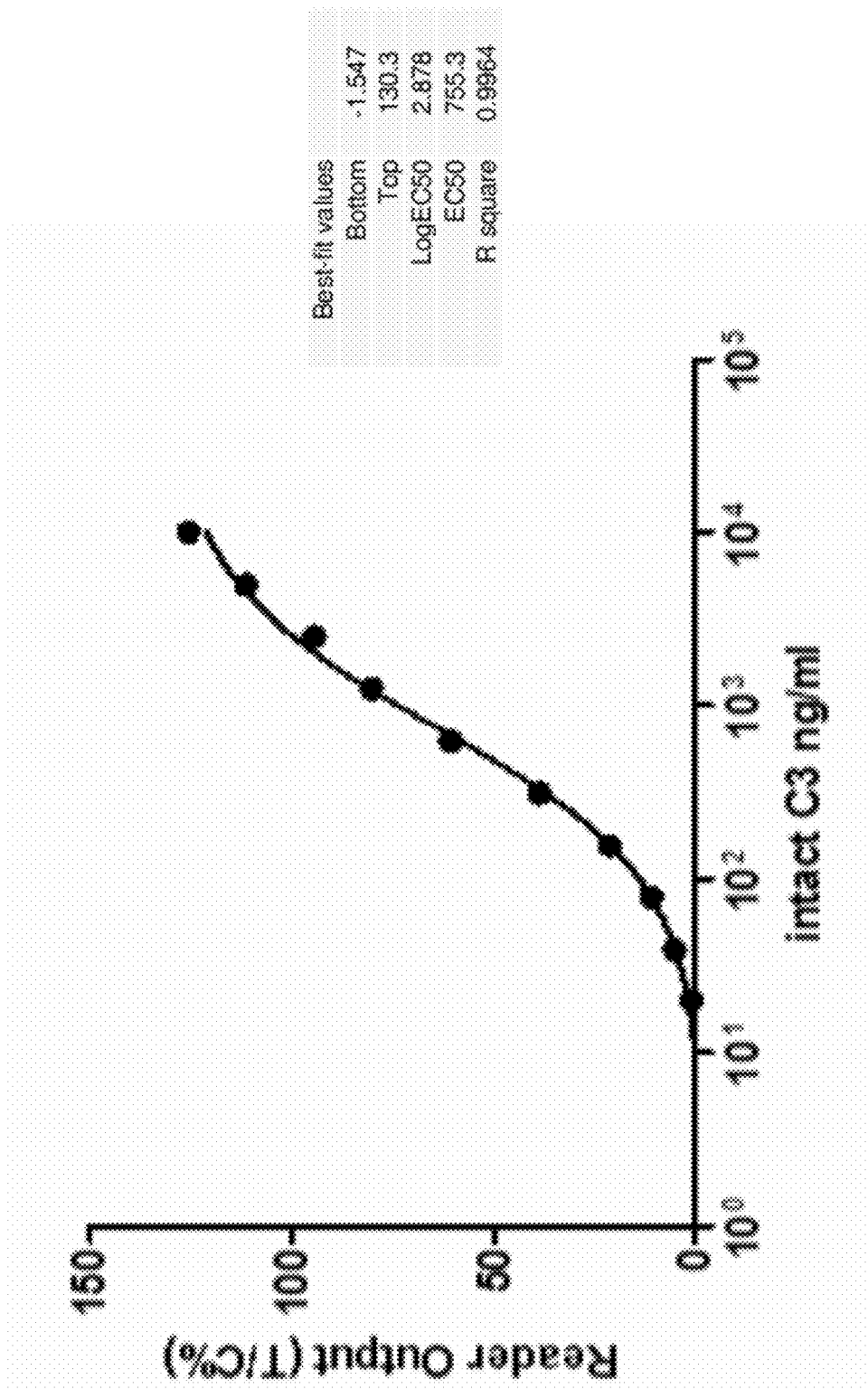
FIG. 13 shows sensitivity of a lateral flow immunoassay for intact C3 described herein. Sensitivity ranges from 20 ng/ml to 10 ug/ml. Standard error is less than 3% at 20 minutes. R square=0.9964. Values were verified by ELISA. Error bars are shown, but are smaller than the plotted points.

After the experiment is completed, data was plotted using GraphPad Prism 5 software. The standard curve fits the three-parameter logistic equation: $Y=\text{Bottom} + (\text{Top} - \text{Bottom})/(1 + EC50/X)$. See FIG. 13.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A lateral flow immunoassay for the point-of-care detection of a marker of complement activation in a body fluid sample comprising complement proteins, the lateral flow immunoassay comprising:
   a membrane strip;
   a detecting antibody that binds a first epitope of the marker;
   a test line comprising a capturing antibody that binds a second epitope of the marker; and
   a control line comprising an antibody that binds a control analyte,
   wherein the marker is iC3b.

2. The lateral flow immunoassay of claim 1, wherein the detecting antibody comprises a label that provides a signal.

3. The lateral flow immunoassay of claim 1, wherein the second epitope is a region in the C3d domain which is present on iC3b.

4. The lateral flow immunoassay of claim 1, wherein the marker is iC3b and the first epitope is a neoepitope on iC3b which is revealed when C3b is deactivated to iC3b and which is occluded when iC3b is further degraded to C3c and C3dg.

5. The lateral flow immunoassay of claim 4, wherein the second epitope is a neoepitope present only on C3b, iC3b, and C3dg.

6. The lateral flow immunoassay of claim 1, wherein the body fluid is selected from the group consisting of whole blood, serum, plasma, urine, tears, saliva, wound exudate, bronchoalveolar lavage fluid, and cerebrospinal fluid.

7. The lateral flow immunoassay of claim 1, wherein the control analyte is IgG.

8. The lateral flow immunoassay of claim 1, wherein complement in the body fluid sample is not substantially activated experimentally by the lateral flow immunoassay.

9. The lateral flow immunoassay according to claim 1 for the point-of-care detection of markers of complement activation in a body fluid sample comprising complement proteins, the lateral flow immunoassay further comprising:
   a second detecting antibody that binds a first epitope of a second marker;
   a second test line comprising a second capturing antibody that binds a second epitope of a second marker; and
   at least one control line comprising an antibody that binds a control analyte,
   wherein the second marker is intact C3.

10. The lateral flow immunoassay of claim 9, wherein the first and second detecting antibodies each comprise a label that provides a signal.

11. The lateral flow immunoassay of claim 9, wherein the body fluid is selected from the group consisting of whole blood, serum, plasma, urine, tears, and cerebrospinal fluid.

12. The lateral flow immunoassay of claim 9, wherein the control analyte is IgG.

13. The lateral flow immunoassay of claim 9, wherein complement in the body fluid sample is not substantially activated experimentally by the lateral flow immunoassay.

14. The lateral flow immunoassay of claim 9, wherein the first epitope of intact C3 is a C3a domain which is present on intact C3 and which is lost upon activation of C3.

15. The lateral flow immunoassay of claim 9, wherein the second epitope of intact C3 is a region in the C3d domain which is present on intact C3, C3b, iC3b, and C3d.

16. The lateral flow immunoassay of claim 9, wherein the first epitope of iC3b is a neoepitope on iC3b which is revealed when C3b is deactivated to iC3b and which is occluded when iC3b is further degraded to C3c and C3dg.

17. The lateral flow immunoassay of claim 9, wherein the second epitope of iC3b is a neoepitope present only on C3b, iC3b, and C3dg.

18. The lateral flow immunoassay of claim 9, wherein the antibodies that bind intact C3 and the antibodies that bind iC3b are not substantially cross-reactive.

19. A method for monitoring an individual who is receiving treatment for a physiological condition and who is suffering from a complement-associated disorder, the method comprising:
   (a) obtaining serial samples of a body fluid from the individual;
   (b) determining a complement activation level in each of said samples via the point-of-care lateral flow immunoassay of claim 1;
   (c) comparing the complement activation levels in the serial samples to detect a change in a complement activation level over time; and
   (d) modifying treatment for the individual, based on the correlating of step (c).

20. A method for treating an individual at risk for a complement-associated disorder, the method comprising:
   (a) obtaining a sample of a body fluid from the individual;
   (b) measuring a complement activation level in the sample via the point-of-care lateral flow immunoassay of claim 1;
   (c) correlating the complement activation level in the sample to a risk of a complement-associated disorder by comparing the complement activation level in the sample to a reference level in a control, wherein a deviation in complement activation level in the sample compared to the reference level in the control indicates the individual is at risk for a complement-associated disorder;
   (d) selecting a treatment for the individual, based on the correlating of step (c); and
   (e) treating the individual with the treatment selected in accordance with step (d).

21. The method of claim 20, wherein the complement-associated disorder is selected from the group consisting of trauma, inflammatory distress, autoimmune disorders, intracranial hemorrhage, infection, transplant rejection, ocular disease, heart disease, ischemia/reperfusion injury, age-related macular degeneration, paroxysmal nocturnal hemoglobinuria (PNH), hereditary angioedema, renal disease, pregnancy-associated disorders, and neurological disorders.

22. The method of claim 21, wherein the inflammatory distress is selected from the group consisting of organ failure, systemic inflammatory response syndrome (SIRS), adult respiratory distress syndrome (ARDS), sepsis, and pneumonia.

23. The method of claim 20, wherein the body fluid is selected from the group consisting of whole blood, serum, plasma, urine, tears, saliva, wound exudate, bronchoalveolar lavage fluid, and cerebrospinal fluid.

24. The method of claim 20, wherein the lateral flow immunoassay detects the presence or absence of one or more of intact C3 and iC3b in the sample.

25. The method of claim 20, wherein the treatment comprises performing additional testing on the individual, optimizing a ventilator, or administering a therapeutic agent selected from the group consisting of antibiotics, anti-inflammatory agents, and inhibitors of complement.

26. The method of claim 25, wherein the additional testing comprises obtaining a broncheoalveolar lavage (BAL) sample from the individual.

27. The method of claim 25 wherein the inhibitor of complement is selected from the group consisting of natural complement inhibitors and derivatives thereof, compstatin and analogs thereof, anti-membrane attack complex (MAC) antibodies, anti-C3 antibodies, anti-05 antibodies, C3a receptor antagonists, and C5a receptor antagonists.

28. The method of claim 20, wherein the point-of-care lateral flow immunoassay provides a measurement of the amount of iC3b and further comprises measurement of the amount of intact C3 and/or total C3 in the sample in about 30 minutes or less.

* * * * *